(12) United States Patent
Kjeldsen et al.

(10) Patent No.: US 12,035,897 B2
(45) Date of Patent: Jul. 16, 2024

(54) TISSUE COLLECTION DEVICE FOR COLLECTION OF TISSUE SAMPLES FROM A BIOPSY NEEDLE AND BIOPSY DEVICE INCLUDING TISSUE COLLECTION DEVICE

(71) Applicant: TeesuVac ApS, Hørsholm (DK)

(72) Inventors: Ole Kjeldsen, Struer (DK); John Hvidkjær, Hørsholm (DK); Tue Kjærgaard Toft, Copenhagen (DK)

(73) Assignee: TeesuVac ApS, Hørsholm (DK)

( * ) Notice: Subject to any disclaimer, the term of this patent is extended or adjusted under 35 U.S.C. 154(b) by 857 days.

(21) Appl. No.: 15/734,620

(22) PCT Filed: Jun. 4, 2019

(86) PCT No.: PCT/EP2019/064446
§ 371 (c)(1),
(2) Date: Dec. 3, 2020

(87) PCT Pub. No.: WO2019/233992
PCT Pub. Date: Dec. 12, 2019

(65) Prior Publication Data
US 2021/0153850 A1    May 27, 2021

(30) Foreign Application Priority Data
Jun. 4, 2018   (EP) .................................... 18175771

(51) Int. Cl.
*A61B 10/00*      (2006.01)
*A61B 10/02*      (2006.01)
(52) U.S. Cl.
CPC ...... *A61B 10/0096* (2013.01); *A61B 10/0266* (2013.01); *A61B 2010/0225* (2013.01)

(58) Field of Classification Search
CPC ............................................. A61B 2010/0225
See application file for complete search history.

(56) References Cited

U.S. PATENT DOCUMENTS

| 5,526,822 A | 6/1996 | Burbank |
| 2003/0198574 A1 | 10/2003 | Studer |

(Continued)

FOREIGN PATENT DOCUMENTS

| WO | WO 2007/112751 A2 | 10/2007 |
| WO | WO 2018/087367 A2 | 5/2018 |
| WO | WO 2018/127848 A1 | 7/2018 |

OTHER PUBLICATIONS

International Search Report and Written Opinion of International Searching Authority for Application No. PCT/EP2019/064446, mailed Jul. 5, 2019 (11 pages).

*Primary Examiner* — Matthew Kremer
(74) *Attorney, Agent, or Firm* — Nixon Peabody LLP

(57) ABSTRACT

A tissue collection device including a biopsy needle support arrangement to support a biopsy needle so that a tissue compartment in the biopsy needle may be located at a collection position. The tissue collection device includes a carrier medium adapted to adhere to and carry a tissue sample deposited thereon and adapted to be arranged at a deposition position permanently spaced from the collection position. The tissue collection device includes a swiping element adapted to swipe sideward relative to the longitudinal direction through the tissue compartment located at the collection position and in the direction of the deposition position in order to thereby move a tissue sample from the tissue compartment to the carrier medium and to thereby press the tissue sample onto the carrier medium so that the tissue sample is deposited on the carrier medium.

19 Claims, 16 Drawing Sheets

(56) References Cited

U.S. PATENT DOCUMENTS

| | | |
|---|---|---|
| 2005/0215921 A1 | 9/2005 | Hibner |
| 2009/0227893 A1* | 9/2009 | Coonahan .......... A61B 10/0283 600/566 |
| 2012/0065542 A1* | 3/2012 | Hibner ................ A61B 10/0275 600/567 |
| 2015/0148686 A1* | 5/2015 | Baym ................. A61M 35/003 600/572 |
| 2015/0223787 A1 | 8/2015 | Coonahan |
| 2016/0242748 A1 | 8/2016 | Pasternak |
| 2017/0311935 A1 | 11/2017 | Choung |
| 2019/0321009 A1* | 10/2019 | Nevo ................. A61B 10/0096 |

* cited by examiner

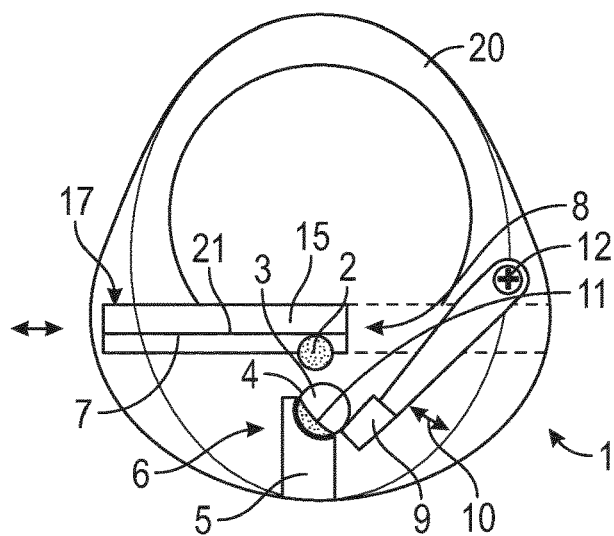

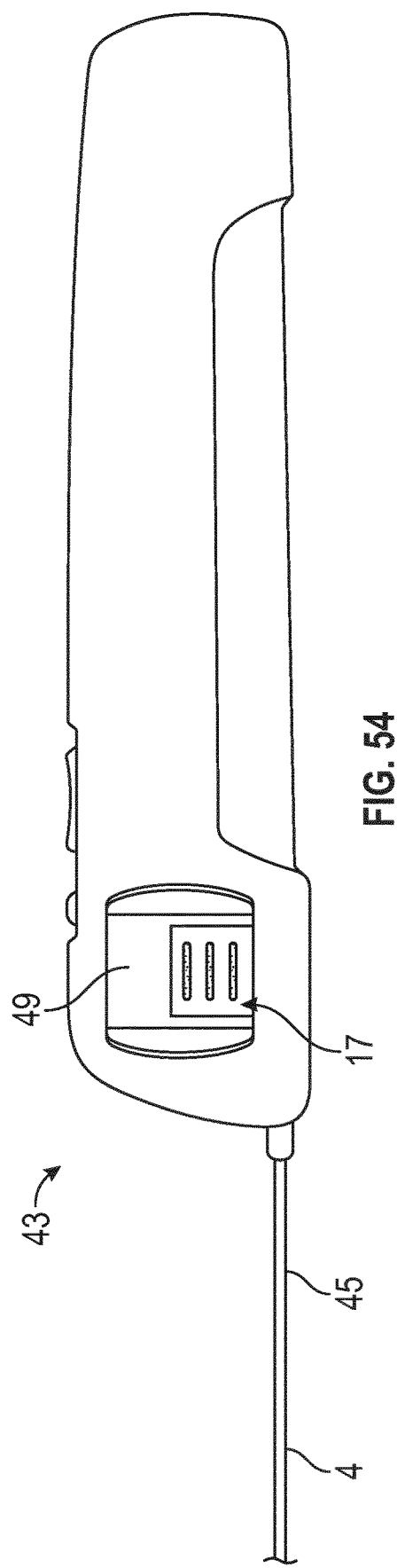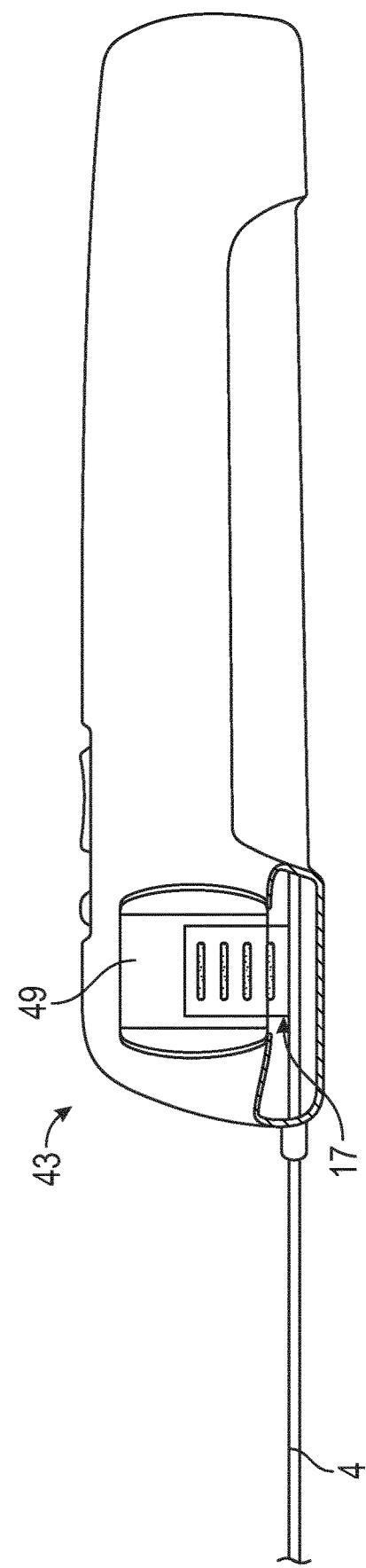

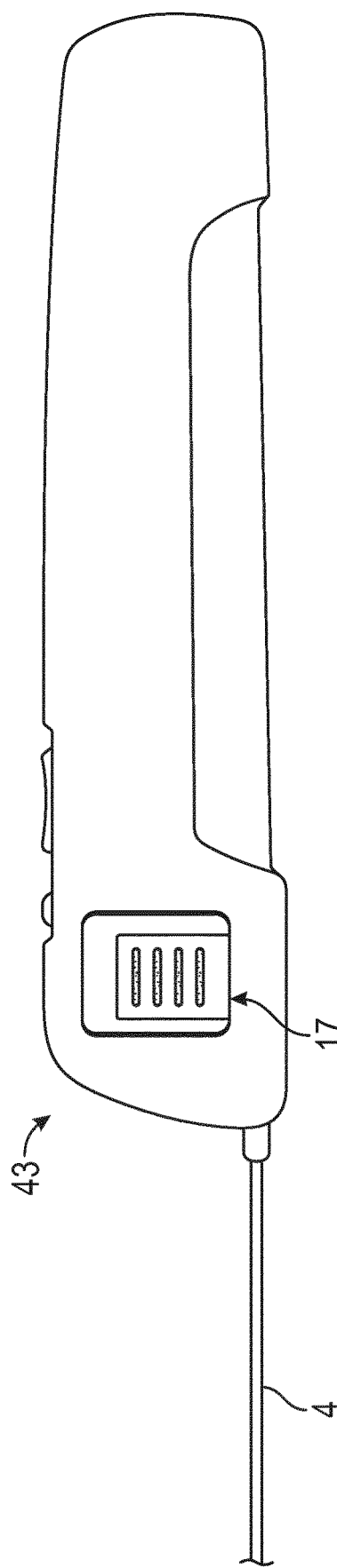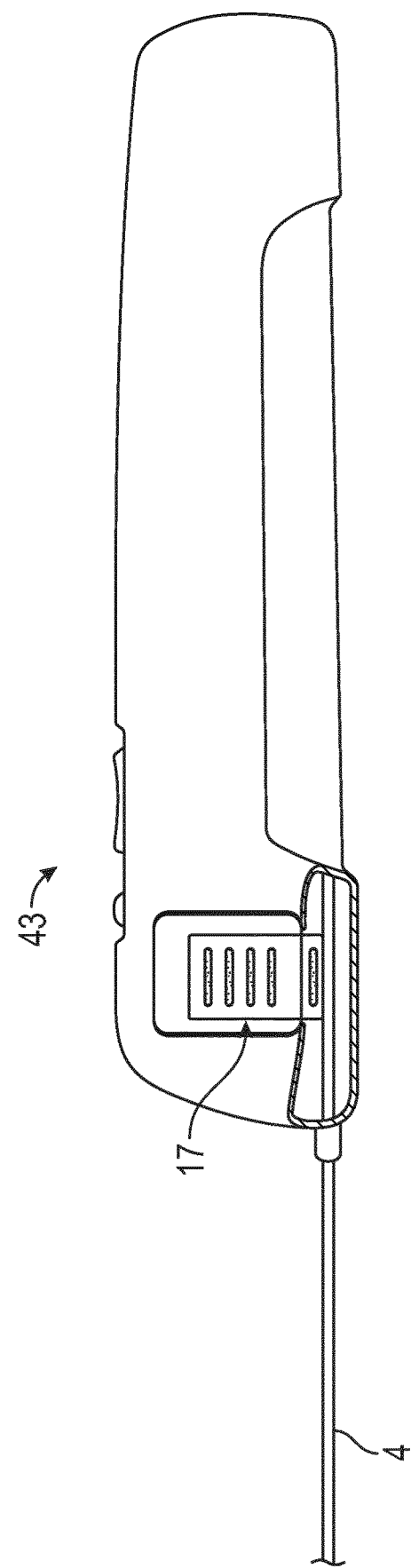

TISSUE COLLECTION DEVICE FOR COLLECTION OF TISSUE SAMPLES FROM A BIOPSY NEEDLE AND BIOPSY DEVICE INCLUDING TISSUE COLLECTION DEVICE

CROSS-REFERENCE TO RELATED APPLICATIONS

This application is a U.S. National Stage of International Application No. PCT/EP2019/064446, filed Jun. 4, 2019, which claims the benefit of European Patent Application No. 18175771.7, filed Jun. 4, 2018, both of which are incorporated herein by reference in their entireties.

The present invention relates to a tissue collection device for collection of one or more tissue samples from a tissue compartment of a biopsy needle, the tissue collection device including a biopsy needle support arrangement adapted to support a biopsy needle so that a tissue compartment extending in a longitudinal direction in the biopsy needle may be located at a collection position, and the tissue collection device including a carrier medium adapted to adhere to and carry a tissue sample deposited thereon, the tissue collection device being adapted to advance a carrier medium holder after each deposition of a tissue sample on a part of the carrier medium, so that the deposited tissue sample is moved away on said part of the carrier medium from a deposition position and a fresh part of the carrier medium is moved to the deposition position.

US 2016/0242748 A1 discloses a tissue collection device in which a lever provided with a sample holder in the form of a cassette is displaceable so that a sample sheet of the cassette may contact and adhere to a tissue sample in the biopsy needle. By subsequently displacing the lever and cassette away from the biopsy needle, the tissue sample may be removed from the biopsy needle. The cassette may be provided with two sample windows in the form of through-openings in a cassette cover, and the cassette may be assembled with the sample sheet fixed in place between a cassette base and the cassette cover. Thereby the sample sheet is prevented from displacement in the cassette, and each window allows view and access to a portion of the sample sheet from the cassette cover side. The cassette may be arranged displaceably in a transverse direction of the lever so that a sample may be positioned on the sample sheet through each window. However, the operation of this tissue collection device is rather cumbersome and does not facilitate fast collection of a larger number of tissue samples. Furthermore, the device is rather bulky.

WO 2007/112751 A2 discloses a biopsy gun with an integrated tissue collection device. In a first embodiment, the tissue collection device has the form of a rotatable drum having tissue storage chambers along its periphery. A wall of each tissue storage chamber forms a wedge-shaped lifting edge adapted to lift a tissue sample from a tissue chamber of a biopsy needle and into the tissue storage chamber when the drum is rotated. Firstly, the tissue sample is lifted up from the tissue chamber of the biopsy needle by means of a row of pins which are pressed up through holes in the biopsy needle. Subsequently, the drum is rotated, whereby the pins pass through grooves of the wedge-shaped lifting edge. In another embodiment, the tissue collection device has the form of a rotatable drum and a central tissue storage chamber. The rotatable drum has peripherally arranged scooping elements adapted to lift tissue samples out of the tissue chamber of a biopsy needle in the longitudinal direction of the biopsy needle, whereby the drum rotates about an axis extending at right angles to the biopsy needle. However, the biopsy gun described in this document is rather bulky and does not facilitate easy handling of the tissue samples after collection. In particular, the rotatable drum forming the tissue storage may be too bulky for preliminary X-ray examination of the tissue samples.

U.S. Pat. No. 5,526,822 A discloses a method and apparatus for automated biopsy and collection of soft tissue by means of vacuum. A tissue sample cassette has the form of a flat block in which a number of cylindrical tissue sample chambers are arranged in parallel and mutually spaced. The tissue sample cassette may be displaced transversely in relation to a biopsy needle in order to place tissue samples successively in the tissue sample chambers. The tissue samples are by means of vacuum transported into the cylindrical tissue sample chambers in the longitudinal direction of the chambers. However, the apparatus described in this document is rather bulky and does not facilitate easy handling of the tissue samples after collection.

US 2003/0198574 A1 discloses an apparatus for handling biopsy specimens and preparing these for immediate high-pressure freezing. A biopsy specimen introduced into an opening of a biopsy needle is centred over a specimen well of a preparation plate made of a material with good thermal conductivity, such as a metal, preferably copper, brass, titanium or aluminium. By lowering a cylindrical shaped part with a tip, the biopsy specimen is then released from the opening of the biopsy needle and falls into the specimen well. The apparatus is manually operated and rather bulky. In addition, in order to operate correctly, the apparatus has to be arranged on a table or the like in order to maintain a stable position and orientation.

The object of the present invention is to provide a compact tissue collection device facilitating collection of tissue samples.

In view of this object, the deposition position is permanently spaced from the collection position, the tissue collection device includes a swiping element adapted to swipe sideward relative to the longitudinal direction through the tissue compartment located at the collection position and in the direction of the deposition position in order to thereby move a tissue sample from the tissue compartment to the carrier medium and to thereby press the tissue sample onto the carrier medium so that the tissue sample is deposited on the carrier medium.

Thereby, by pushing the tissue sample from the tissue compartment to the carrier medium and pressing the tissue sample onto the carrier medium by means of a swiping element only needing to travel a limited distance, a very simple and repeatable operation of the tissue collection device is possible in a very compact device. Moreover, by pressing the tissue sample onto the carrier medium, the orientation of the carrier medium in relation to the tissue compartment of the biopsy needle is not important. For example, the carrier medium may just as well be positioned above the tissue compartment as below the tissue compartment. Pressing the tissue sample onto the carrier medium may in any case ensure that the tissue sample adheres to and is maintained on the carrier medium.

In an embodiment, the swiping element is adapted to swipe back and forth through the tissue compartment. Thereby, successive tissue samples may be collected from the tissue compartment of the biopsy needle.

In an embodiment, the swiping element has the form of an elastic blade. Thereby, the elasticity of the swiping element may limit a possible pressure applied to the tissue sample by the swiping element when depositing the tissue sample on the carrier medium and thereby contribute to a gentler deposition of the tissue sample. Furthermore, the swiping element may better wipe the tissue compartment and thereby possibly remove residues otherwise remaining after the deposition of a tissue sample on the carrier medium.

In an embodiment, the swiping element is adapted to wipe a bottom wall of the tissue compartment as it swipes through the tissue compartment. Thereby, the swiping element may possibly remove residues otherwise remaining after the deposition of a tissue sample on the carrier medium.

In a structurally particularly advantageous embodiment, the swiping element is arranged pivotally in the tissue collection device.

In an embodiment, a general swiping direction of the swiping element from the collection position and in the direction of the deposition position forms a swiping angle with a general direction of extension of a part of the carrier medium arranged at the deposition position, and the swiping angle is between 30 degrees and 90 degrees. Thereby, a suitable pressure component may be applied in a direction at right angles to said general direction of extension of a part of the carrier medium in order for the tissue sample to be securely deposited on the carrier medium.

Preferably, the swiping angle is between 45 degrees and 90 degrees. Thereby, a relatively larger pressure component may be applied in a direction at right angles to said general direction of extension of a part of the carrier medium so that the tissue sample may be even more securely deposited on the carrier medium.

In an embodiment, the tissue collection device is adapted to place a protective sheet on the corresponding part of the carrier medium after each deposition of a tissue sample and advance the protective sheet with the carrier medium holder so that the deposited tissue samples are sandwiched between the carrier medium and the protective sheet. Thereby, it may be even better ensured that the tissue samples are maintained on the carrier medium.

In an embodiment, the tissue collection device includes a removable carrier medium cassette in which a number of tissue samples may be arranged side by side on the carrier medium in a row extending along an at least substantially straight line or along a curved line. Thereby, the cassette may be removed from the tissue collection device after collection of a number of tissue samples and the cassette may serve to hold the tissue samples when send to a laboratory. If the tissue samples are arranged side by side on the carrier medium in a row extending along an at least substantially straight line or along a slightly curved line, it may be advantageous that the cassette may fit into a rather narrow gap of an X-ray apparatus commonly used for pre-examination of tissue samples before sending the samples to the laboratory.

In an embodiment, the removable carrier medium cassette is arranged on the outside of a housing of the tissue collection device. Thereby, the cassette may be easily accessible for removal.

Preferably, the tissue samples arranged side by side on the carrier medium are visible from outside the housing of the tissue collection device. Thereby, each tissue sample may be visibly examined just after taking the sample.

In an embodiment, the tissue collection device is adapted to gradually advance a sheet of carrier medium into the removable carrier medium cassette as successive tissue samples are deposited on the sheet of carrier medium. Thereby, a very compact tissue collection device may be achieved in that the cassette itself may not necessarily need to move in relation to a housing of the tissue collection device.

Furthermore, the tissue collection device may preferably be adapted to deposit the tissue samples on the sheet of carrier medium outside the removable carrier medium cassette. Thereby, the deposition position may be arranged more freely in relation to the removable carrier medium cassette, whereby an even more compact tissue collection device may be achieved. For instance, the deposition position may not need to be arranged in direct continuation of a row of tissue samples arranged side by side on the carrier medium.

In an embodiment, the advancing direction of the sheet of carrier medium at the deposition position differs from the advancing direction of the sheet of carrier medium at a carrier medium inlet opening of the removable carrier medium cassette by at least 90 degrees, and preferably by at least 120 degrees. Thereby, the deposition position may be arranged so to say behind or in front of a row of tissue samples arranged side by side on the carrier medium. Thereby, an even more compact tissue collection device may be achieved.

In a structurally particularly advantageous embodiment, the carrier medium holder is fixed on a leading edge of the sheet of carrier medium and is removable from the tissue collection device together with the removable carrier medium cassette, and the carrier medium holder is adapted to engage releasably with an advance mechanism arranged in the tissue collection device. Thereby, a compact cassette and easy handling may be achieved in that the advance mechanism may be arranged in a housing of the tissue collection device.

In an embodiment, the removable carrier medium cassette has the form of a chain composed by a number of mutually hinged cassette compartments each being adapted to receive a single tissue sample. Thereby, although each tissue sample may be located in a separate cassette compartment, the removable carrier medium cassette may be adapted to receive a relatively large number of tissue samples and the tissue collection device may still be very compact, because the chain forming the removable carrier medium cassette may be entirely or partly rolled up inside a housing of the tissue collection device.

Preferably, neighbouring hinged cassette compartments are adapted to lock together by means of a snap-lock type mechanism in a straight hinge position so that the entire chain of mutually hinged cassette compartments may be locked in a position in which the chain forms an at least substantially straight line. Thereby, the removable carrier medium cassette may be removed from a housing of the tissue collection device in the form of a relatively flat cassette, whereby it may be advantageous that the cassette may fit into a rather narrow gap of an X-ray apparatus commonly used for pre-examination of tissue samples before sending the samples to the laboratory.

In an embodiment, the tissue collection device is adapted to store at least a part of the chain forming the removable carrier medium cassette in an at least partly rolled-up state. Thereby, although each tissue sample may be located in a separate cassette compartment, the removable carrier medium cassette may be adapted to receive a relatively large number of tissue samples and the tissue collection device may still be very compact.

In a structurally particularly advantageous embodiment, the cassette compartments are mutually hinged by means of a flexible hinge, such as a living hinge.

In a structurally particularly advantageous embodiment, each cassette compartment has a gripper along a first side and a corresponding protrusion along a second side, and the gripper of a first cassette compartment is adapted to grip over a corresponding protrusion of a second cassette compartment. Thereby, neighbouring hinged cassette compartments may be adapted to lock together in a straight hinge position so that the entire chain of mutually hinged cassette compartments may be locked in a position in which the chain forms an at least substantially straight line.

In a structurally particularly advantageous embodiment, each cassette compartment has the form of a channel in which the carrier medium may extend. Thereby, a good separation between neighbouring tissue samples may be achieved.

In an embodiment, the channel of each cassette compartment is covered by means of a sheet of carrier medium. Thereby, a good adhesion between the tissue samples and the carrier medium may be achieved.

In an embodiment, the sheet of carrier medium is adapted to be pressed at least further into the channel at deposition of a tissue sample. Thereby, it may be ensured that a suitable pressure is applied by the swiping element between the tissue sample and the carrier medium so that an even better adhesion between the tissue samples and the carrier medium may be achieved.

In an embodiment, the channel of each cassette compartment is covered by means of a separate sheet of carrier medium. Thereby, relative movement between neighbouring cassette compartments may be facilitated in that the carrier medium may not interfere with said relative movement.

In an embodiment, the separate sheet of carrier medium is fixed along at least one wall of the channel by means of adhesion, such as by means of glue. In a structurally particularly advantageous embodiment, In an embodiment, at least one free edge of the separate sheet of carrier medium is held in place in the channel by a corresponding protrusion arranged at a corresponding wall of the channel. Thereby, the separate sheet of carrier medium may be held in place in the channel in a removable manner at least along said protrusion.

In an embodiment, all the channels of the cassette compartments are covered by means of a single common sheet of carrier medium. Thereby, the production of the removable carrier medium cassette may be facilitated in that the single common sheet of carrier medium may be applied to the cassette in a continuous manner.

In an embodiment, the single common sheet of carrier medium forms a bulge or crease between neighbouring hinged cassette compartments. Thereby, relative movement between neighbouring cassette compartments may be facilitated in that the carrier medium may not be stretched out at the hinges between neighbouring cassette compartments.

In an embodiment, the carrier medium includes or is formed by a paper material, such as biopsy paper. Thereby, a stable attachment of the tissue samples on the carrier medium may be achieved.

In an embodiment, the biopsy needle support arrangement is adapted to support the biopsy needle relative to a housing of the tissue collection device in a fixed position in a transverse direction of the biopsy needle.

The invention furthermore relates to a biopsy device including a tissue collection device as described above. Thereby, by integrating the tissue collection device in a biopsy device, the whole process of taking a number of tissue samples from a patient and collecting the tissue samples in the tissue collection device may be automated and thereby facilitated and improved by being more consistent.

In an embodiment, the biopsy device has a housing and a biopsy needle extending from the housing and including an outer cutting needle and an inner needle with a tissue compartment for receiving a tissue sample, the outer cutting needle surrounds the inner needle and is arranged slidingly along the inner needle, the outer cutting needle has a cutting end distant from the housing and a sample opening or sample end inside the housing at a distance from the cutting end, the inner needle is slidable in relation to the housing so that the tissue compartment is displaceable between the cutting end of the outer cutting needle and the sample opening or sample end of the outer cutting needle, and the tissue collection device is arranged in the housing at the sample opening or sample end of the outer cutting needle. Thereby, the outer cutting needle may be retained inserted in the tissue of the patient during the taking of more samples which may be particularly advantageous for instance when taking tissue samples from the prostate whereby the gut may otherwise be penetrated once for every tissue sample taken. Because the tissue sample is collected by the tissue collection device from the sample opening or sample end of the outer cutting needle which sample opening or sample end is located at an opposite end of the outer cutting needle in relation to the cutting end of the outer cutting needle, the cutting end of the outer cutting needle may remain inside the tissue of the patient during the taking of several tissue samples which are sequentially transported one by one longitudinally through the outer cutting needle by longitudinal displacement of the inner needle with a tissue sample located in the tissue compartment.

In an embodiment, the biopsy device is adapted to arrange the inner needle in a rotational collection position when the inner needle is so displaced in relation to the housing of the biopsy device that the tissue compartment is located at the sample opening or sample end of the outer cutting needle for collection of a tissue sample, and the rotational collection position corresponds to a general swiping direction of the swiping element from the collection position and in the direction of the deposition position. Thereby, it may be ensured that a general swiping direction of the swiping element from the collection position and in the direction of the deposition position forms a suitably swiping angle with a general direction of extension of a part of the carrier medium arranged at the deposition position. Thereby, a suitable pressure component may be applied in a direction at right angles to said general direction of extension of a part of the carrier medium in order for the tissue sample to be securely deposited on the carrier medium.

The invention will now be explained in more detail below by means of examples of embodiments with reference to the very schematic drawing, in which FIG. 1 is a cross-sectional view of an embodiment of a biopsy device and tissue collection device according to the invention;

FIG. 2 is an exploded view seen from below of the biopsy device and tissue collection device of FIG. 1;

FIG. 3 is a cross-sectional end view of an embodiment of a removable carrier medium cassette of the biopsy device illustrated in FIG. 4;

FIG. 4 is a cross-sectional view of another embodiment of a biopsy device and tissue collection device according to the invention, incorporating the removable carrier medium cassette of FIG. 3;

FIG. 54 is a side view of an embodiment of a biopsy device with integrated tissue collection device corresponding to the embodiment of FIG. 48, whereby a removable carrier medium cassette with a flat, transparent lid has been mounted on a side of the device;

FIG. 55 is another side view of the biopsy device with integrated tissue collection device of FIG. 54, whereby part of the device has been cut away, thereby illustrating the entire sheet of carrier medium inside the device;

FIG. 56 is a side view of an embodiment of a biopsy device with integrated tissue collection device, whereby a removable carrier medium cassette with a rounded, transparent lid has been mounted on a side of the device;

FIG. 57 is another side view of the biopsy device with integrated tissue collection device of FIG. 56, whereby part of the device has been cut away, thereby illustrating the entire sheet of carrier medium inside the device;

Figure 58:
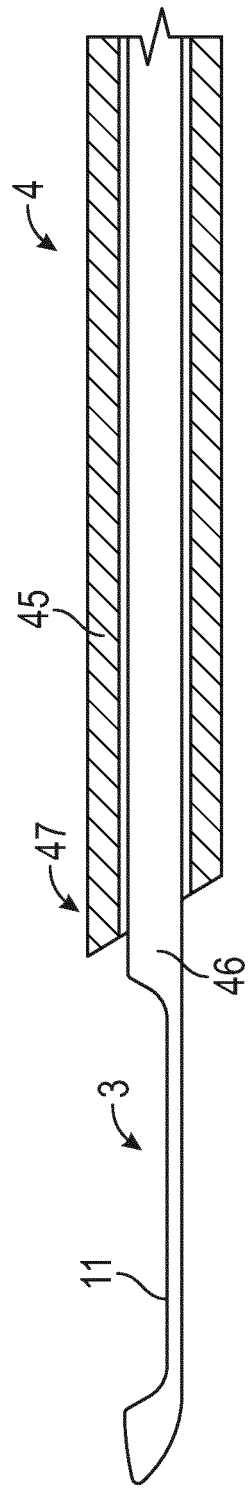
Figure 59:
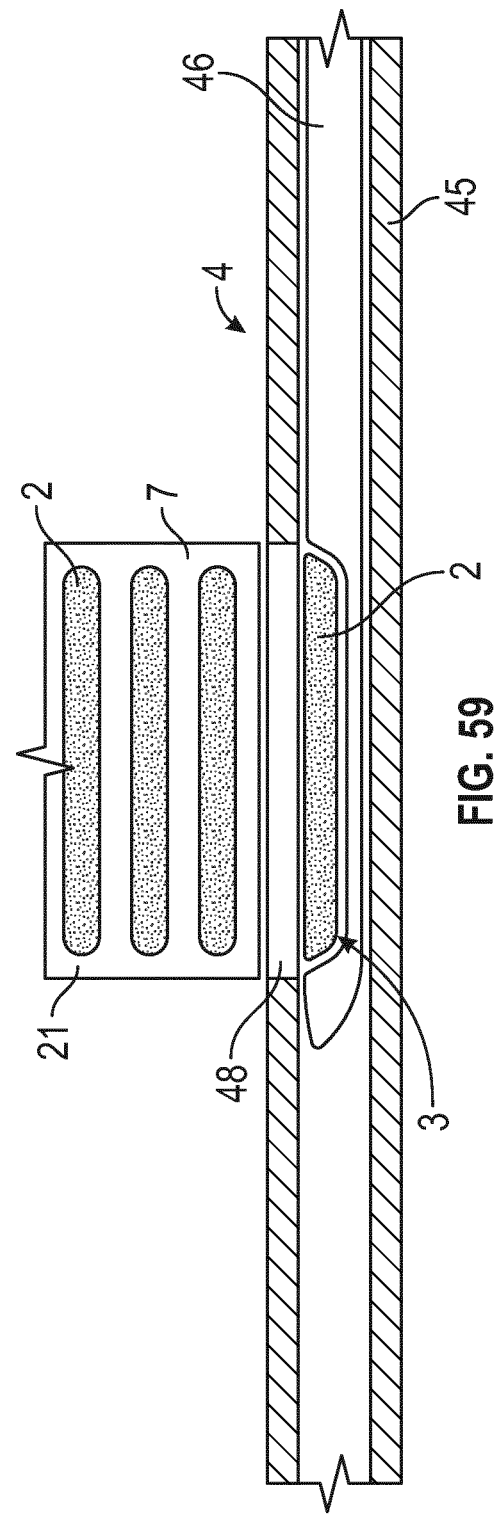

FIG. 58 is a partial axial cross-section of a cutting end of an outer cutting needle of a biopsy needle, whereby a tissue compartment of an inner needle of the biopsy needle is located outside the cutting end of the outer cutting needle; and FIG. 59 is a partial axial cross-section of a sample opening of the outer cutting needle of the biopsy needle of FIG. 58, whereby the tissue compartment of the inner needle of the biopsy needle is located at the sample opening.

FIG. 1 shows a tissue collection device 1 for collection of one or more tissue samples 2 from a tissue compartment 3 of a biopsy needle 4. The tissue collection device includes a biopsy needle support arrangement 5 adapted to support a biopsy needle 4 so that a tissue compartment 3 extending in a longitudinal direction in the biopsy needle 4 may be located at a collection position 6. In the illustrated embodiment, the biopsy needle support arrangement 5 forms a rounded cavity in which the biopsy needle 4 may rest and thereby be correctly positioned in the collection position 6. For simplicity, an outer needle of the biopsy needle 4 is not illustrated in the figure.

The tissue collection device 1 further includes a carrier medium 7 adapted to carry a tissue sample 2 deposited thereon and adapted to be arranged at a deposition position 8 permanently spaced from the collection position 6. In order to move a tissue sample 2 from the tissue compartment 3 to the carrier medium 7 so that the tissue sample 2 is deposited on the carrier medium 7, the tissue collection device 1 includes a swiping element 9 adapted to swipe sideward 10 relative to the longitudinal direction through the tissue compartment 3 located at the collection position 6 and in the direction of the deposition position 8. Thereby, during swiping, the swiping element 9 moves gradually closer to the deposition position 8 and thereby pushes the tissue sample 2 to the deposition position 8. FIG. 2 illustrates an exploded view of part of the tissue collection device 1 of FIG. 1, seen from below.

The swiping element 9 is furthermore adapted to press the tissue sample 2 onto the carrier medium 7. In order to press the tissue sample 2 onto the carrier medium 7, the swiping element 9 may be adapted to swipe through the tissue compartment 3 and stop at a certain distance from the carrier medium 7 positioned at the deposition position 8, wherein said certain distance is smaller than, preferably at least 10 percent smaller than and most preferred at least 25 percent smaller than a diameter of an inner needle 46 of the biopsy needle 4. Thereby, it may be ensured that the tissue sample 2 is deformed slightly when pressing it onto the carrier medium 7, and consequently, a suitable pressured between the tissue sample 2 and the carrier medium 7 may be obtained in order for the tissue sample 2 to stick onto the carrier medium 7. Alternatively, the swiping element 9 may be adapted to swipe so fast through the tissue compartment that sufficient momentum is transferred to the tissue sample in order for the tissue sample to move and hit the carrier medium 7 with such a speed that it is pressed onto the carrier medium 7.

It is noted that in the embodiments of the invention illustrated, when the tissue collection device 1 or biopsy device 43 is held in a typical operational orientation, the carrier medium 7 at the deposition position 8 is positioned above or obliquely upward in relation to the tissue compartment 3 of the biopsy needle 4. This is possible due to the fact that the swiping element 9 is adapted to press the tissue sample 2 onto the carrier medium 7 so that the tissue sample 2 is deposited on the carrier medium 7 regardless of the orientation of the tissue collection device 1 or biopsy device 43 and regardless of the orientation of the carrier medium 7 in relation to the tissue compartment 3. As a result, as seen for instance in FIGS. 42, 43, 48, 49, 54 to 57, the biopsy needle 4 may be positioned in the housing 20 of the tissue collection device 1 or the housing 44 of the biopsy device 43 very close to a side wall of the housing. This has the advantage that the biopsy needle 4 may be inserted for instance into the tissue of a breast close to the chest surface and at an angle more or less parallel to the chest surface. However, according to the invention, the carrier medium 7 at the deposition position 8 may also be positioned below the tissue compartment 3 of the biopsy needle 4. In the context of this description above and below refers to the positions contemplated when the tissue collection device 1 or biopsy device 43 is held in a typical or in an intended operational orientation.

The carrier medium 7 is adapted to adhere to a tissue sample 2. This may for instance be achieved if the carrier medium 7 is or includes biopsy paper.

In an embodiment of the invention, the carrier medium includes a liquid absorbing material. Thereby, because a tissue sample typically has a high content of fluid, it may be ensured that the tissue sample may adhere to the carrier medium.

In an embodiment of the invention, the carrier medium has a porous sample contacting surface. Thereby, because a tissue sample typically has a high content of fluid, it may be ensured that the tissue sample may adhere to the carrier medium.

In the illustrated embodiment, the swiping element 9 is arranged pivotally 12 in a housing 20 of tissue collection device 1. However, the swiping element 9 may also be arranged displaceably, for instance slidingly in a track or in a number of tracks.

In the illustrated embodiment, the swiping element 9 is adapted to swipe back and forth between the collection position 6 and the deposition position 8 through the tissue compartment 3 in order to collect successive tissue samples from the tissue compartment of the biopsy needle. The carrier medium 7 may be replaced between successive depositions of tissue samples, or, as it will be further explained below, the carrier medium 7 may be displaced between successive depositions of tissue samples.

The swiping element 9 may have the form of an elastic blade, whereby a possible pressure applied to the tissue sample 2 by the swiping element 9 when depositing the tissue sample 2 on the carrier medium 7 may be limited, and thereby contribute to a gentler deposition of the tissue sample 2. Furthermore, the swiping element 9 may better wipe the tissue compartment 3 and thereby possibly remove possible residues otherwise remaining after the deposition of a tissue sample 2 on the carrier medium 7. In addition, the swiping element 9 may be adapted to wipe a bottom wall 11 of the tissue compartment 3 as it swipes through the tissue compartment 3. This may be achieved for instance by the swiping element 9 being elastic and bending slightly when touching the bottom wall 11 of the tissue compartment 3 or by the swiping element 9 being adapted to very accurately pass close to the bottom wall 11. In the embodiment illustrated in FIG. 2, the swiping element 9 is composed by a swiping blade 64 and two lever arms 65 connecting each end of the swiping blade 64 with the pivotal arrangement 12, that is, the two lever arms are mounted pivotally about the pivotal axis 12. In this case, the swiping element 9 may be elastic by the swiping blade 64 being elastic or by the two lever arms 65 being elastic, or both the swiping blade 64 and the two lever arms 65 may be elastic. The swiping element 9 may for instance be made of plastic or any other suitable material.

Alternatively or additionally, the swiping element 9 may be elastically driven, which may also contribute to a gentler deposition of the tissue sample 2. The swiping element 9 may suitably be driven by a spring force obtained by manual operation of the device or by means of an electric motor.

Alternatively, the swiping element 9 may have the form of one single blade arranged pivotally or on a rotatable drum or spindle. Similarly, the swiping element 9 may have the form of a number of blades or other suitable elements arranged on a rotatable drum or spindle. If the swiping element 9 or elements is/are arranged on a rotatable drum or spindle, the spindle may rotate stepwise in one direction of rotation so that it rotates a certain angular distance after each deposition of a tissue sample 2.

As seen in FIG. 2, preferably the swiping element 9 has the form of a swiping blade 64 or the like extending in at least almost substantially the full length of the tissue compartment 3 in the longitudinal direction of the biopsy needle 4.

The tissue collection device 1 is adapted to advance a carrier medium holder 15 in the form of a removable carrier medium cassette 17 after each deposition of a tissue sample 2 on a part of the carrier medium 7, so that the deposited tissue sample 2 is moved away from the deposition position 8 on said part of the carrier medium 7 and a fresh part of the carrier medium is moved to the deposition position 8. As seen, in the removable carrier medium cassette 17, a number of tissue samples 2 may be arranged side by side on the carrier medium 7 in a row extending along an at least substantially straight line.

FIG. 4 shows a modified embodiment of the tissue collection device 1 illustrated in FIGS. 1 and 2. The embodiment illustrated in FIG. 4 is further provided with a roll of protective sheet 16, and the tissue collection device 1 is adapted to place the protective sheet 16 on the corresponding part of the carrier medium 7 after each deposition of a tissue sample 2 and advance the protective sheet 16 with the carrier medium holder 15 so that the deposited tissue samples 2 are sandwiched between the carrier medium 7 and the protective sheet 16. As it is further seen, in this embodiment, the carrier medium 7 is arranged in a waveform so that tissue samples 2 may be located in the troughs of the waveform. Thereby, a larger contact area between the carrier medium 7 and the tissue samples 2 may be achieved which may result in better adhesion between the carrier medium 7 and the tissue samples 2. It is noted that generally throughout the description, relative sizes and relative distances are not necessarily illustrated realistically, because the figures are only schematic, so that for instance the tissue samples 2 may in reality be thicker than that illustrated.

As further illustrated in FIG. 4, a general swiping direction 13 of the swiping element 9 from the collection position 6 and in the direction of the deposition position 8 forms a swiping angle A with a general direction 14 of extension of a part of the carrier medium 7 arranged at the deposition position 8. The swiping angle A may be between 30 degrees and 90 degrees, and preferably between 45 degrees and 90 degrees. Thereby, a suitable pressure component may be applied in a direction at right angles to said general direction 14 of extension of a part of the carrier medium 7 in order to ensure that the tissue sample 2 be securely deposited on the carrier medium 7.

Figures 5, 6:
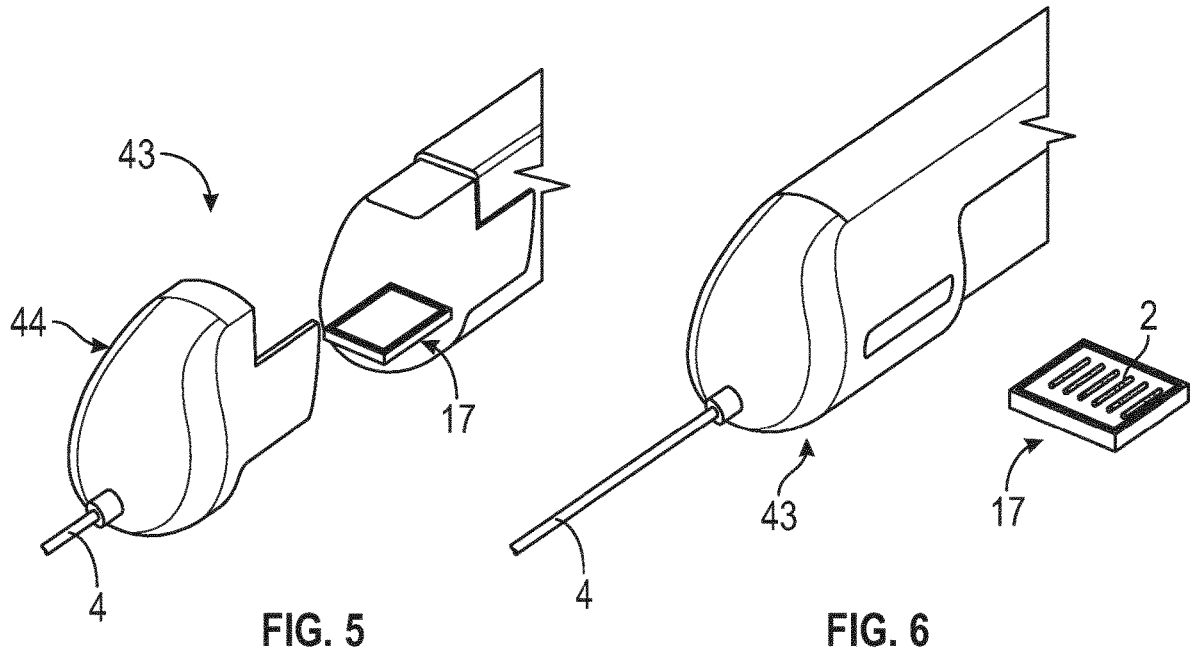
FIG. 5 is an exploded perspective view of part of an embodiment of a biopsy device with integrated tissue collection device according to the invention, whereby the removable carrier medium cassette has been inserted into the device.
FIG. 6 is a perspective view of part of the biopsy device with integrated tissue collection device of FIG. 5, whereby the removable carrier medium cassette has been taken out of the device.

FIG. 5 illustrates the position of the removable carrier medium cassette 17 inside a housing 44 of a biopsy device 43 incorporating a tissue collection device 1 of the type illustrated in FIGS. 1 to 4. However, when the tissue collection device 1 is integrated into a biopsy device 43 provided with a biopsy needle 4, the biopsy needle support arrangement 5 illustrated in FIG. 1 is replaced by a biopsy needle support arrangement 5 formed by the housing 44 or other component of the biopsy device 43 in that the biopsy needle 4 is mounted and thereby supported in the housing 44 in a manner known per se. Furthermore, it is noted that in FIG. 5, the housing 20 of the tissue collection device 1 is also the housing 44 of the biopsy device 43. In any case, the biopsy needle support arrangement 5 is adapted to support the biopsy needle 4 relative to the housing 20 of the tissue collection device 1 in a fixed position in a transverse direction of the biopsy needle 4.

FIG. 6 illustrates the removable carrier medium cassette 17 outside the housing 44 of the biopsy device 43, whereby the removable carrier medium cassette 17 has been turned upside down.

Figures 7, 8:
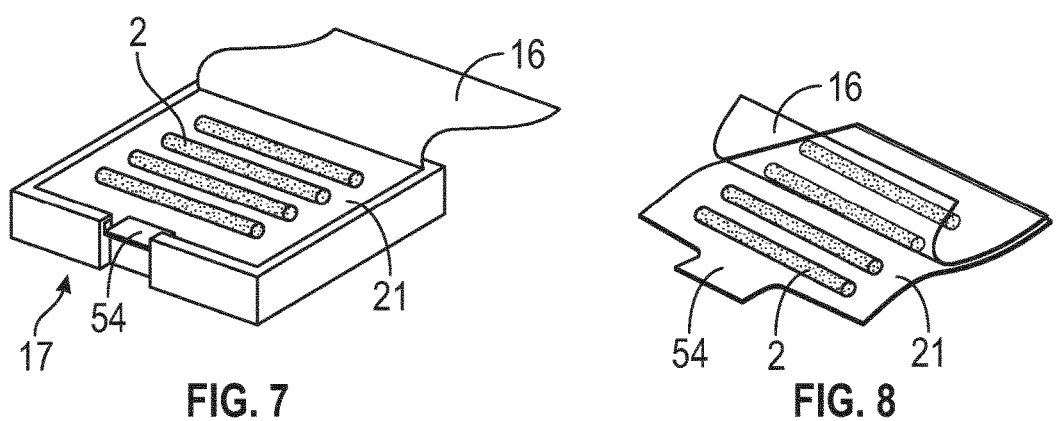
FIG. 7 is a perspective view of another embodiment of the removable carrier medium cassette according to the invention.
FIG. 8 is a perspective view of a sheet of carrier medium with protective sheet which has been removed from the removable carrier medium cassette of FIG. 7.
Figure 9:
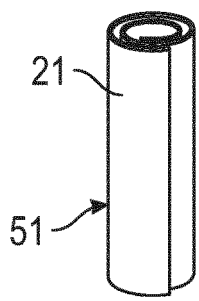
FIG. 9 is a perspective view of the sheet of carrier medium with protective sheet of FIG. 8, whereby the sheet of carrier medium has been rolled up for transport.

FIG. 7 illustrates the removable carrier medium cassette 17 of FIG. 6 whereby the protective sheet 16 has been folded back. FIG. 8 illustrates a sheet 21 of carrier medium 7 with protective sheet 16 attached along an end edge and slightly folded back, whereby the sheet 21 of carrier medium 7 with protective sheet 16 has been removed from the removable carrier medium cassette 17. In this form, the sheet 21 of carrier medium 7 with protective sheet 16 may easily be inserted into a narrow slot of a not shown X-ray device. FIG. 9 illustrates the sheet 21 of carrier medium 7 with protective sheet 16 rolled up for transport. The carrier medium 7, for instance in the form of a paper material, such as biopsy paper, may in the rolled up form be positioned in a container.

In the embodiments illustrated in FIGS. 10 to 27, the removable carrier medium cassette 17 has the form of a chain 27 composed by a number of mutually hinged cassette compartments 28 each being adapted to receive a single tissue sample 2. As seen, the cassette compartments 28 are mutually hinged by means of a flexible hinge 31, such as a living hinge.

Figure 23:
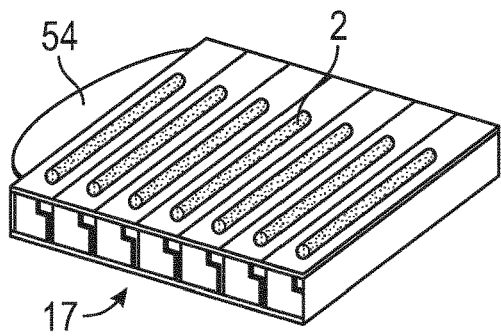
FIG. 23 is a perspective view of yet another embodiment of the removable carrier medium cassette according to the invention.
Figure 24:
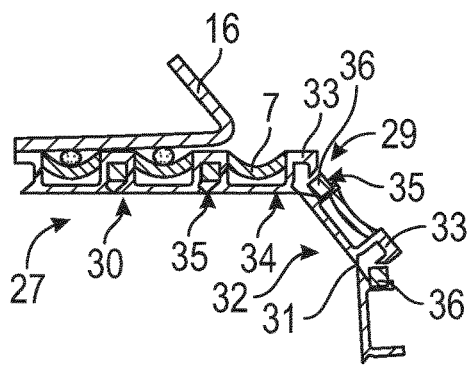
FIG. 24 is a cross-sectional view of the removable carrier medium cassette of FIG. 23, whereby the chain forming the cassette has been partially bent.

Furthermore, in the embodiment illustrated in FIGS. 23 and 24, neighbouring hinged cassette compartments 28 are adapted to lock together by means of a snap-lock type mechanism 29 in a straight hinge position 30 so that the entire chain 27 of mutually hinged cassette compartments 28 may be locked in a position in which the chain 27 forms an at least substantially straight line. As seen, each cassette compartment 28 has a gripper 33 along a first side 34 and a corresponding protrusion 36 along a second side 35, and the gripper 33 of a first cassette compartment 28 is adapted to grip over a corresponding protrusion 36 of a second cassette compartment 28. Each cassette compartment 28 has the form of a channel 37 in which the carrier medium 7 may extend.

Figure 10:
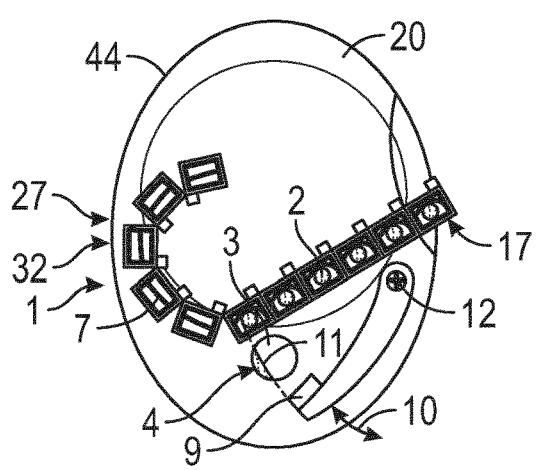
FIG. 10 is a cross-sectional view of yet another embodiment of a biopsy device and tissue collection device according to the invention, incorporating a removable carrier medium cassette of the type illustrated in FIGS. 11 and 12.
Figure 11:
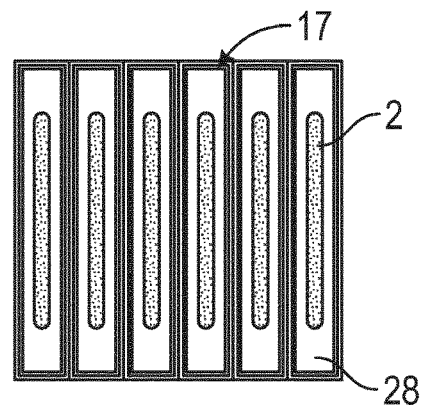
FIG. 11 is a top view of the removable carrier medium cassette of the biopsy device and tissue collection device of FIG. 10.
Figure 12:
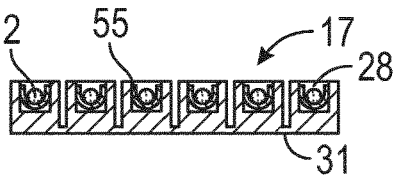
FIG. 12 is a cross-sectional view of the removable carrier medium cassette of FIG. 11.
Figure 13:
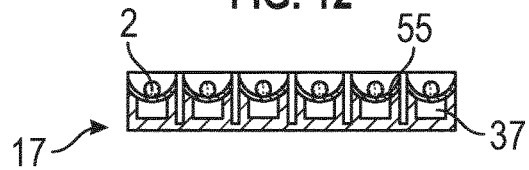
FIGS. 13 and 14 are cross-sectional views corresponding to that of FIG. 12 of different embodiments of the removable carrier medium cassette.
Figure 14:
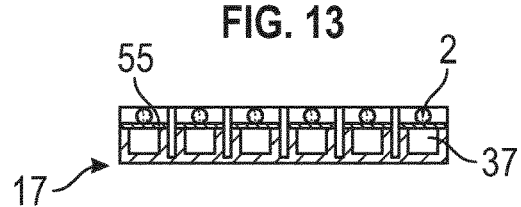
Figure 15:
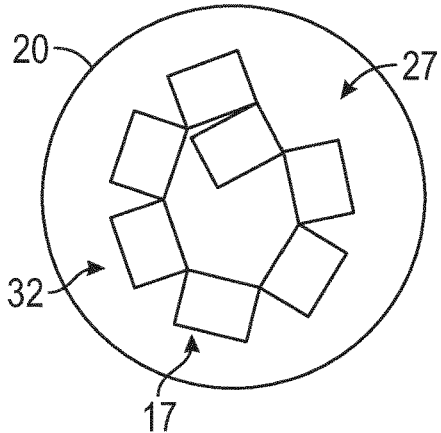
FIG. 15 illustrates an end view of the removable carrier medium cassette of FIG. 10, whereby the chain forming the removable carrier medium cassette has been rolled up.
Figure 16:
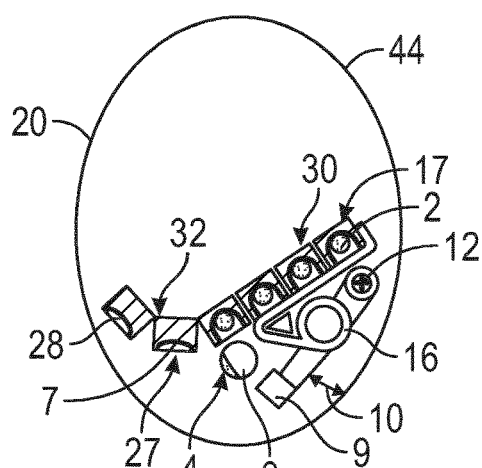
FIG. 16 is a view corresponding to that of FIG. 10, of yet another embodiment of the biopsy device and tissue collection device.
Figure 17:
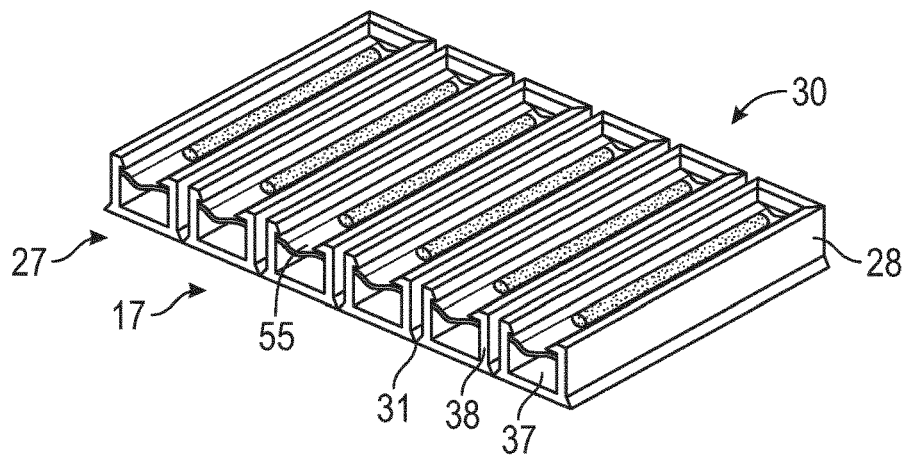
FIG. 17 is a perspective view of yet another embodiment of the removable carrier medium cassette according to the invention.
Figure 18:
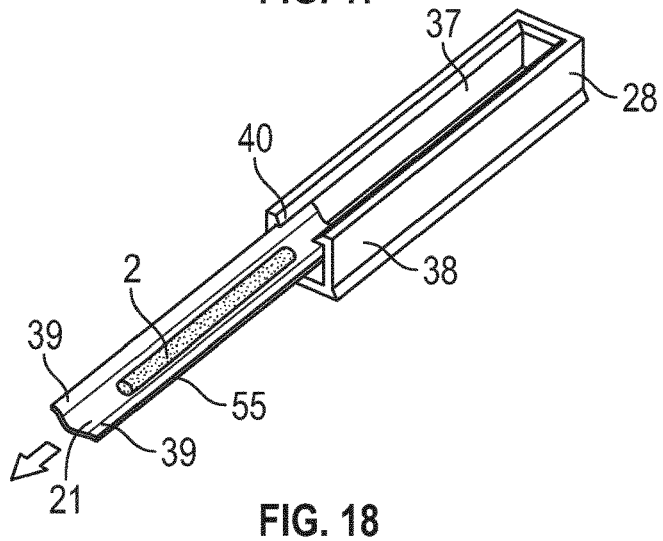
FIG. 18 is a perspective view of a separate cassette compartment of the removable carrier medium cassette of FIG. 17.
Figure 19:
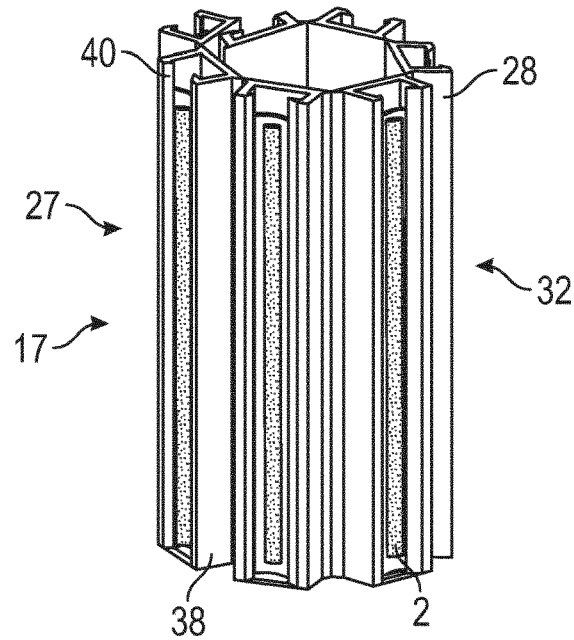
FIG. 19 is a perspective view of the removable carrier medium cassette of FIG. 17, whereby the chain forming the removable carrier medium cassette has been rolled up for transport.
Figure 20:
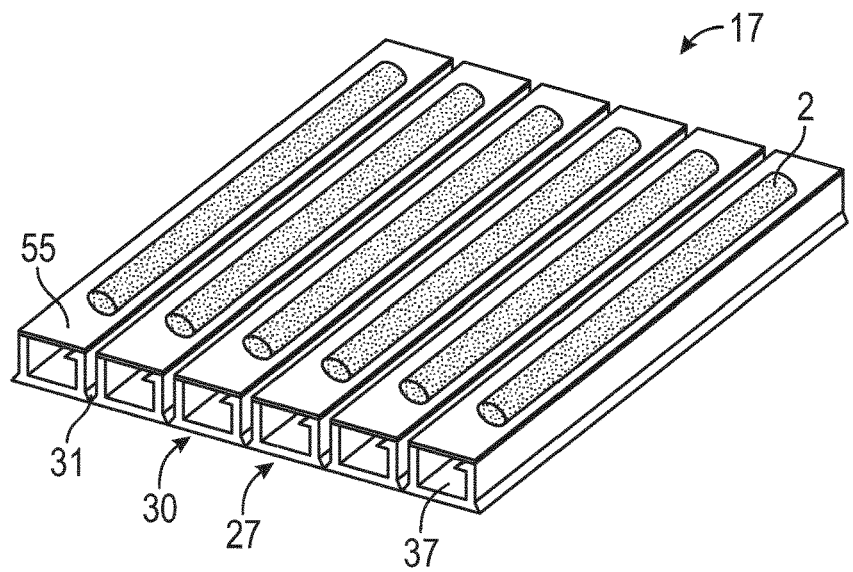
FIG. 20 is a perspective view of yet another embodiment of the removable carrier medium cassette according to the invention.
Figure 21:
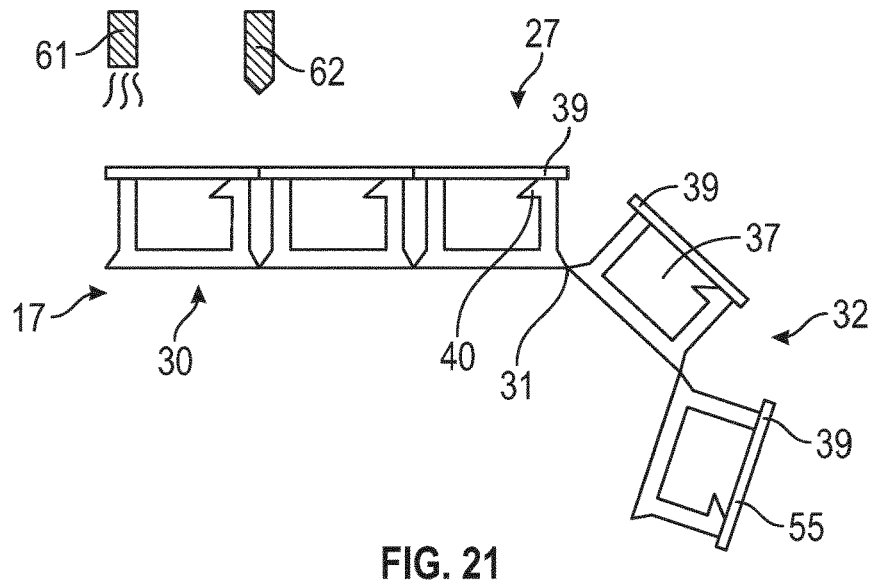
FIG. 21 is an end view illustrating manufacturing steps of the manufacturing of the removable carrier medium cassette of FIG. 20.

In the embodiments illustrated in FIGS. 10 and 16, the tissue collection device 1 is adapted to store a part of the chain 27 forming the removable carrier medium cassette 17 in a partly rolled-up state 32. Thereby, a relatively compact device may contain the entire removable carrier medium cassette 17. On the other hand, when the removable carrier medium cassette 17 has been removed from the housing 20, the hinged cassette compartments 28 may be locked together by means of the snap-lock type mechanism 29 in the straight hinge position 30. Thereby, the removable carrier medium cassette 17 may easily be inserted into a narrow slot of a not shown X-ray device.

As illustrated in the figures, the channel 37 of each cassette compartment 28 is covered by means of a sheet 21 of carrier medium 7 in the form of biopsy paper. As seen for instance in FIG. 16, the sheet 21 of carrier medium 7 may be adapted to be pressed at least further into the channel 37 at deposition of a tissue sample 2.

As illustrated in the FIGS. 12, 13, 14, 17, 18, 19, 20, 21, 22 and 24, the channel 37 of each cassette compartment 28 may be covered by means of a separate sheet 21 of carrier medium 7. This may improve the flexibility of the flexible hinges 31 between neighbouring cassette compartments 28.

Figure 22:
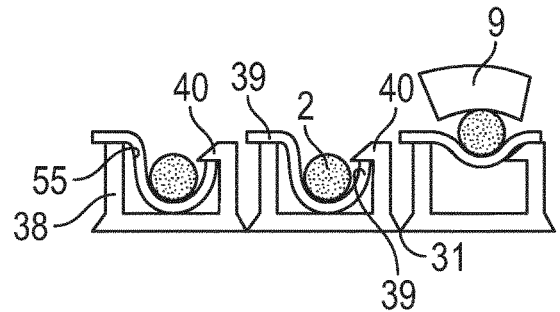
FIG. 22 is a partial end view of a use situation of the removable carrier medium cassette of FIG. 20.

As illustrated in FIG. 22, a free edge 39 of the separate sheet 21 of carrier medium 7 may be fixed along one wall 38 of the channel 37 by means of adhesion, such as by means of glue, and another free edge 39 of the separate sheet 21 of carrier medium 7 may be held in place in the channel 37 by a corresponding protrusion 40 arranged at a corresponding wall 38 of the channel 37. This may be obtained by a production step illustrated in FIG. 21, whereby a welding tool 61 and a punching tool 62 are employed.

Figure 25:
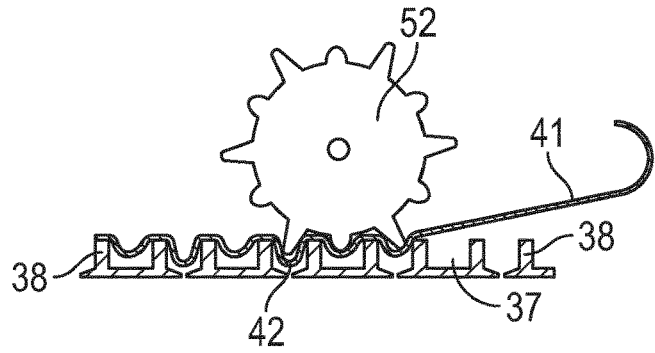
FIG. 25 is a cross-sectional view illustrating a manufacturing step of the manufacturing of a removable carrier medium cassette of FIG. 26.
Figure 26:
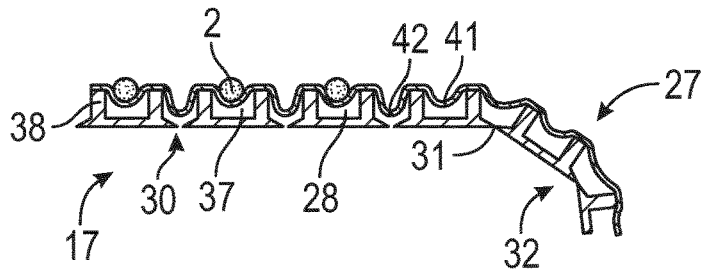
FIG. 26 is a cross-sectional view of the removable carrier medium cassette of FIG. 25 in a partially bent state.
Figure 27:
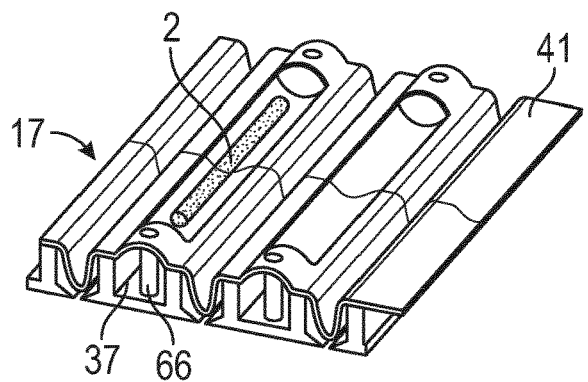
FIG. 27 is a perspective view of a removable carrier medium cassette of a type similar to that of FIG. 26.

In another embodiment illustrated in FIGS. 25 to 27, all the channels 37 of the cassette compartments 28 are covered by means of a single common sheet 41 of carrier medium 7. In order to obtain suitable flexibility of the flexible hinges 31 between neighbouring cassette compartments 28, the single common sheet 41 of carrier medium 7 forms a crease 42 between neighbouring hinged cassette compartments 28. This may be achieved by a production step illustrated in FIG. 25, whereby a spiked wheel 52 of a cassette production apparatus has longer spikes adapted to form the creases 42 and shorter spikes in between the longer spikes adapted to press the sheet 41 of carrier medium 7 slightly down into the channels 37 of the cassette compartments 28. As seen in FIG. 27, the cassette compartments 28 may be provided with pins 66 adapted to engage holes in the single common sheet 41 of carrier medium 7 in order to better hold the sheet onto the cassette compartments.

In the embodiments illustrated in FIGS. 28 to 57, the tissue collection device 1 is adapted to gradually advance a sheet 21 of carrier medium 7 into the removable carrier medium cassette 17 as successive tissue samples 2 are deposited on the sheet 21 of carrier medium 7. As in these illustrated embodiments, it is preferred that the tissue collection device 1 is adapted to deposit the tissue samples 2 on the sheet 21 of carrier medium 7 outside the removable carrier medium cassette 17.

Figure 28:
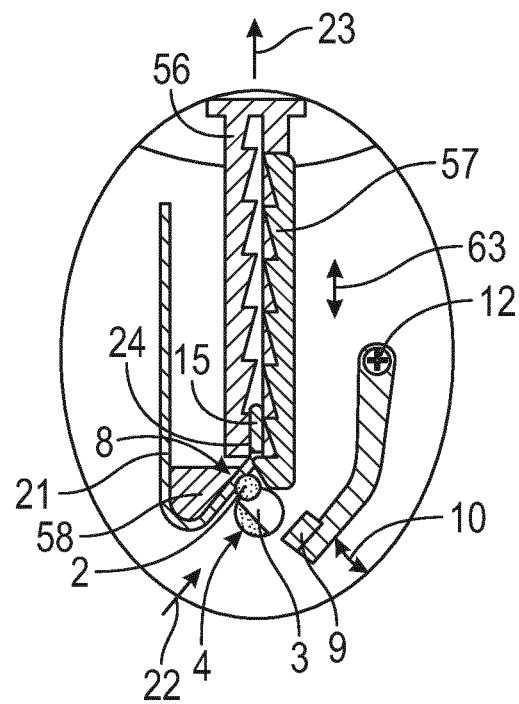
FIG. 28 is a cross-sectional view of yet another embodiment of a biopsy device and tissue collection device according to the invention, incorporating a removable carrier medium cassette of the type illustrated in FIGS. 29 and 30.
Figure 29:
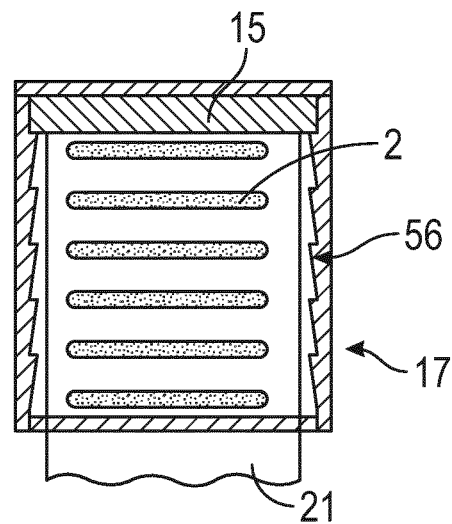
FIG. 29 is a top view of the removable carrier medium cassette of the biopsy device and tissue collection device of FIG. 28.
Figure 30:
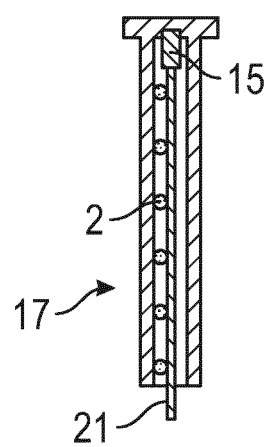
FIG. 30 is a cross-sectional view of the removable carrier medium cassette of FIG. 29.
Figure 31:
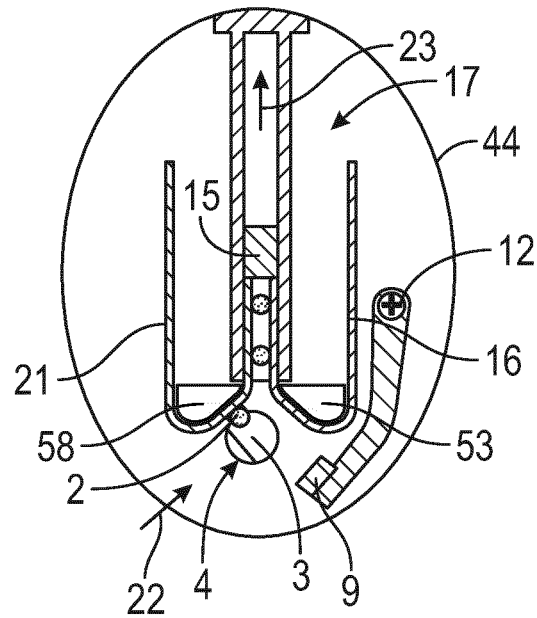
FIG. 31 is a cross-sectional partial view of yet another embodiment of a biopsy device and tissue collection device of the type illustrated in FIG. 28.
Figure 32:
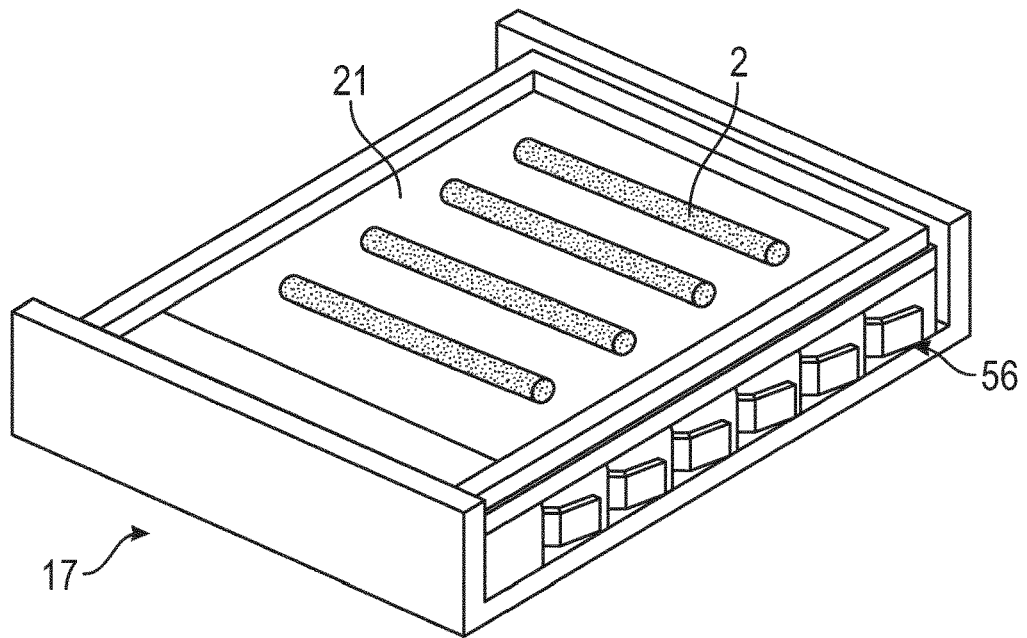
FIG. 32 is a perspective view of yet another embodiment of the removable carrier medium cassette according to the invention.
Figure 33:
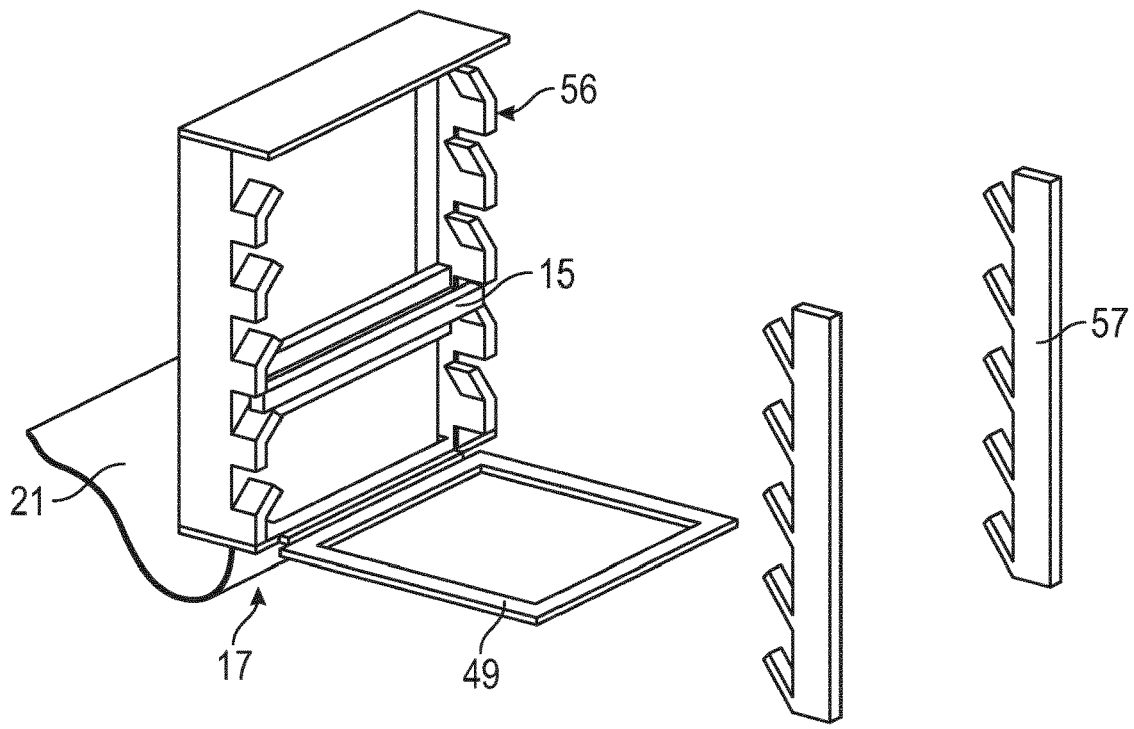
FIG. 33 is an exploded perspective view of the removable carrier medium cassette of FIG. 32.
Figure 34:
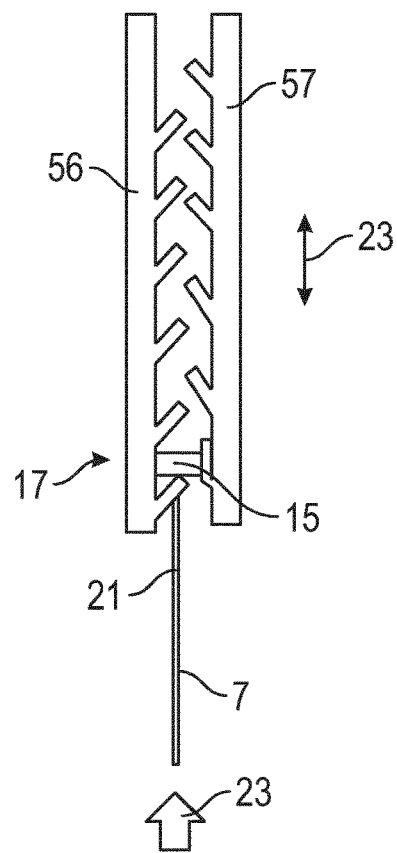
FIG. 34 is an end view of a removable carrier medium cassette of a type similar to that of FIG. 32.

In the embodiments of FIGS. 28 and 31, the advancing direction 22 of the sheet 21 of carrier medium 7 at the deposition position 8 differs from the advancing direction 23 of the sheet of carrier medium at a carrier medium inlet opening 24 of the removable carrier medium cassette 17 by about 45 degrees. However, an even more compact housing 44 of the biopsy device 43 with tissue collection device 1 may be achieved by the embodiments illustrated in FIGS. 44 and 45, wherein the advancing direction 22 of the sheet 21 of carrier medium 7 at the deposition position 8 differs from the advancing direction 23 of the sheet of carrier medium at a carrier medium inlet opening 24 of the removable carrier medium cassette 17 by about 140 degrees.

Figure 35:
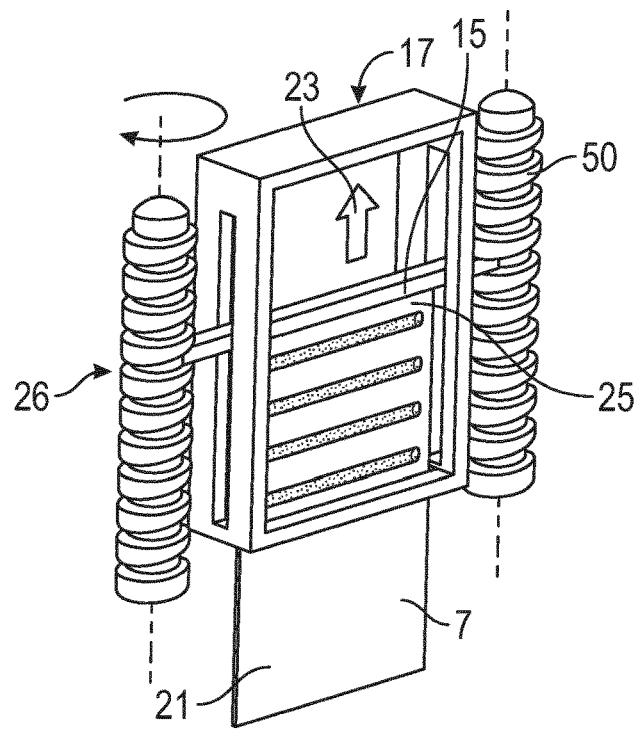
FIG. 35 is a perspective view of yet another embodiment of the removable carrier medium cassette according to the invention, whereby part of a drive mechanism of a biopsy and tissue collection device has been illustrated in engagement with the removable carrier medium cassette.
Figure 38:
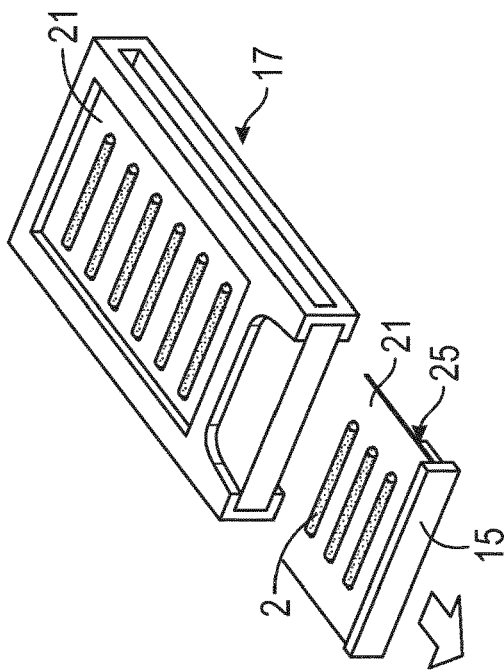
FIG. 38 is a perspective view of the removable carrier medium cassette of the biopsy device with integrated tissue collection device of FIGS. 36 and 37, whereby part of a sheet of carrier medium is illustrated separately.
Figure 41:
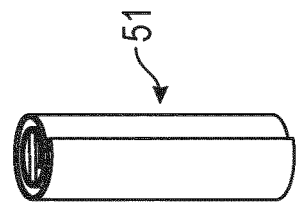
FIG. 41 is a perspective view of the sheet of carrier medium of FIG. 39 in a rolled-up state.
Figure 37:
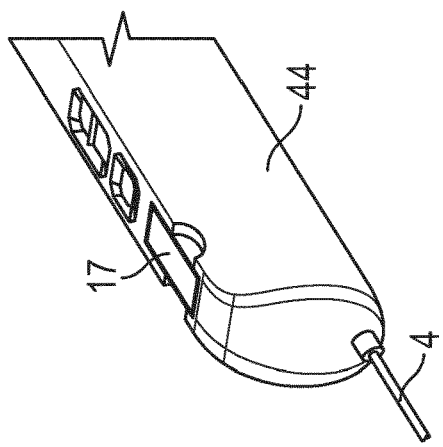
FIG. 37 is a perspective view of the biopsy device with integrated tissue collection device of FIG. 36, whereby the removable carrier medium cassette has been fully inserted into the device.
Figure 40:
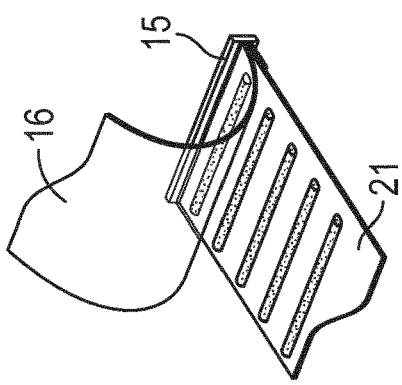
FIG. 40 is a perspective view of the sheet of carrier medium of FIG. 39, whereby the protective sheet has been lifted from the sheet of carrier medium.
Figure 36:
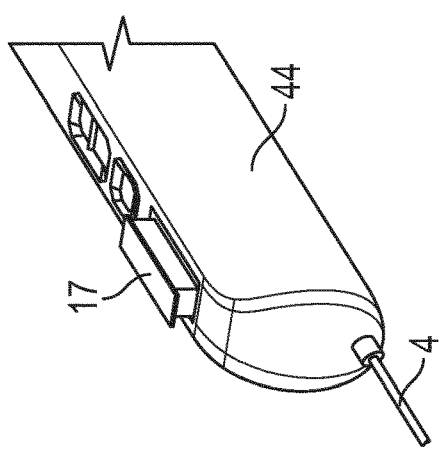
FIG. 36 is a perspective view of part of an embodiment of a biopsy device with integrated tissue collection device, whereby the removable carrier medium cassette extends partly from the device.
Figure 39:
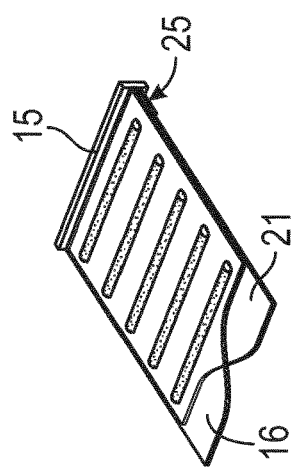
FIG. 39 is a perspective view of a sheet of carrier medium with protective sheet suitable for the removable carrier medium cassette of FIG. 38.
Figure 42:
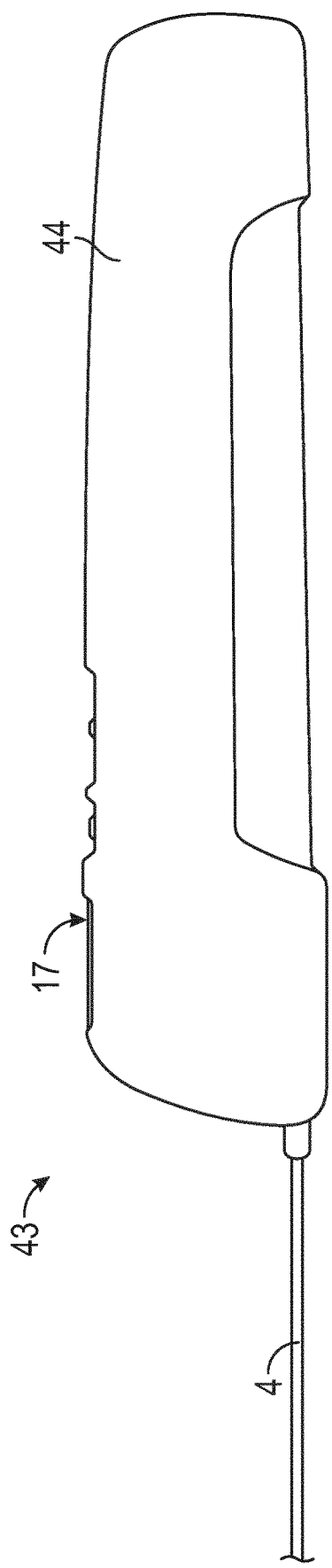
FIG. 42 is a side view of yet another embodiment of a biopsy device with integrated tissue collection device according to the invention, incorporating a removable carrier medium cassette of a type similar to that of FIG. 38.
Figure 43:
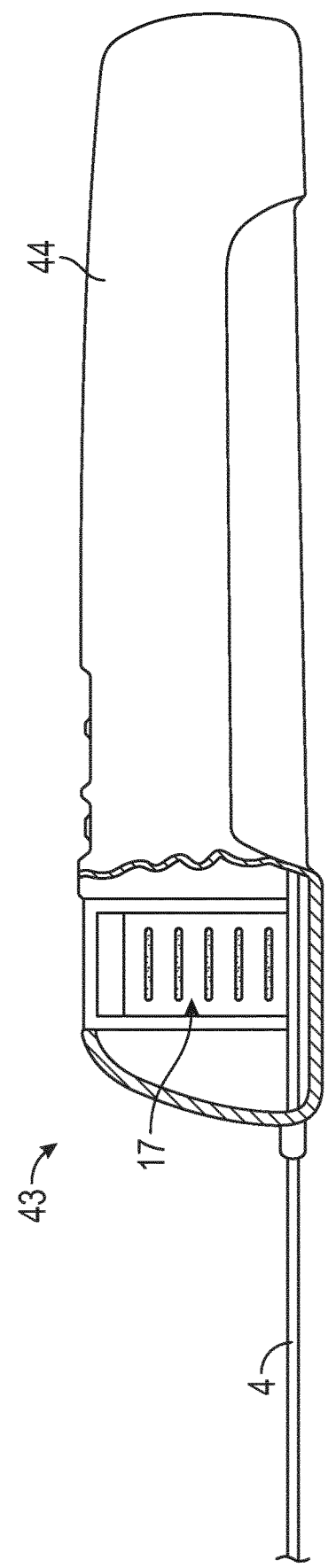
FIG. 43 is another side view of the biopsy device with integrated tissue collection device of FIG. 42, whereby part of the device has been cut away, thereby illustrating the removable carrier medium cassette inserted into the device.
Figure 44:
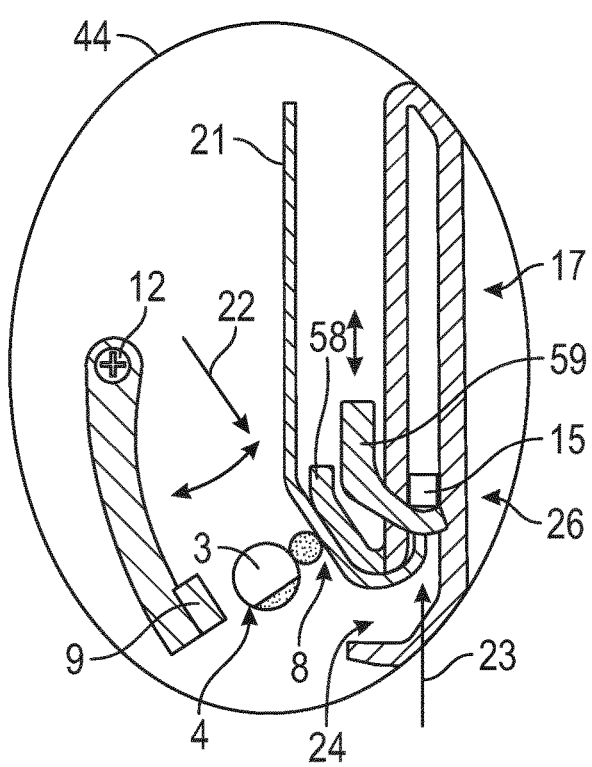
FIG. 44 is a cross-sectional view of yet another embodiment of a biopsy device and tissue collection device according to the invention, incorporating a removable carrier medium cassette.
Figure 45:
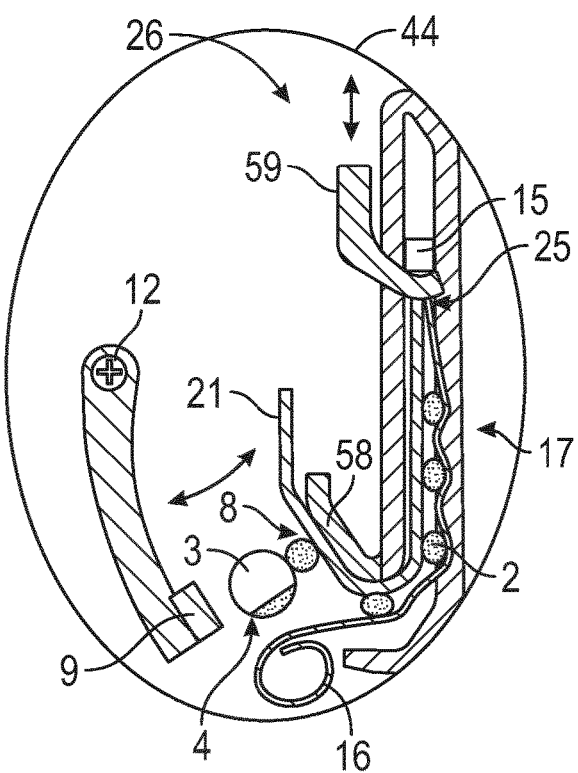
FIG. 45 is a cross-sectional view of an embodiment of the biopsy device and tissue collection device of FIG. 44, whereby the removable carrier medium cassette further incorporates a protective sheet.
Figure 46:
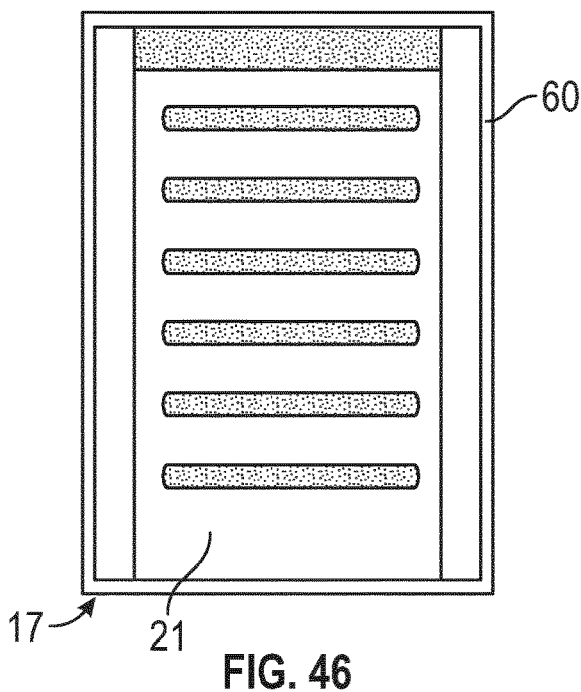
FIG. 46 is a top view of an embodiment of a removable carrier medium cassette according to the invention, whereby the cassette is provided with a rounded, transparent lid.
Figure 47:
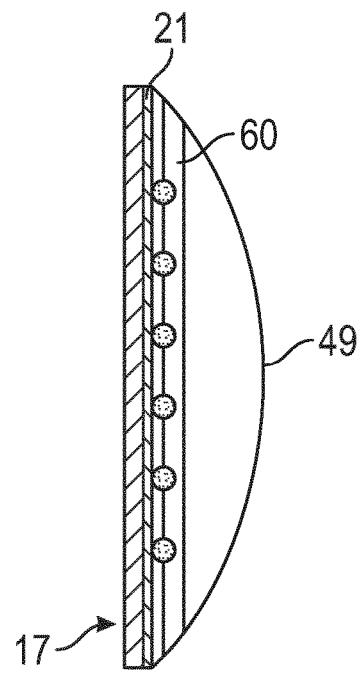
FIG. 47 is a cross-sectional side view of the removable carrier medium cassette of FIG. 46.
Figure 51:
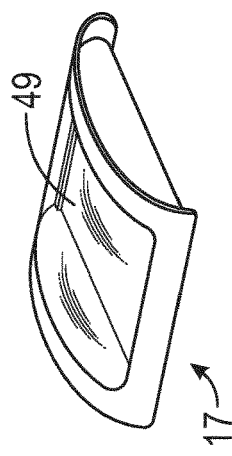
FIG. 51 is a perspective view of the removable carrier medium cassette of the device of FIG. 48, whereby the carrier medium has been removed.
Figure 48:
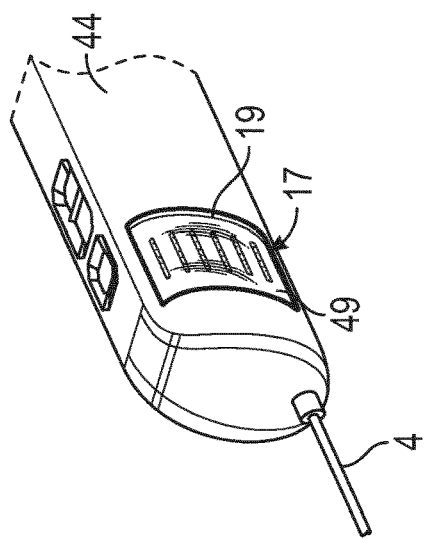
FIG. 48 is a perspective view of part of an embodiment of a biopsy device with integrated tissue collection device, whereby a removable carrier medium cassette with a flat, transparent lid has been mounted on a side of the device.
Figure 52:
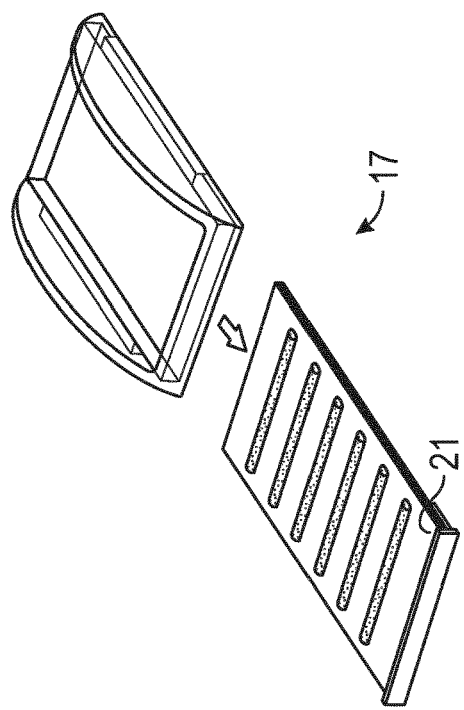
FIG. 52 is a perspective view of a removable carrier medium cassette without a lid, whereby the sheet of carrier medium has been removed and is illustrated separately.
Figure 49:
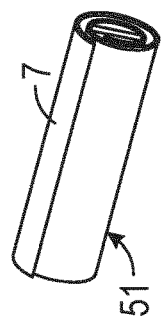
FIG. 49 is a perspective view corresponding to that of FIG. 48 of another embodiment, whereby tissue samples are deposited on a sheet of carrier medium extending slightly curved in a way corresponding to the curvature of a transparent lid of the removable carrier medium cassette.
Figure 50:
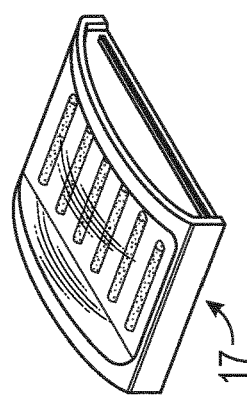
FIG. 50 is a perspective view of the removable carrier medium cassette of the device of FIG. 48, whereby tissue samples have been deposited on the carrier medium.
Figure 53:
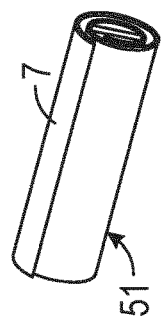
FIG. 53 is a perspective view of the sheet of carrier medium of the cassette of FIG. 52, whereby the sheet of carrier medium has been rolled up.

As for instance seen in FIG. 35, the carrier medium holder 15 may be fixed on a leading edge 25 of the sheet 21 of carrier medium 7 and may be removable from the tissue collection device 1 together with the removable carrier medium cassette 17. The carrier medium holder 15 is in FIG. 35 adapted to engage releasably with an advance mechanism 26 in the form of two spindles 50 arranged in the tissue collection device 1.

In the embodiments illustrated in FIGS. 28, 29, 32, 33 and 34, the advance mechanism 26 has the form of a stationary toothed rack 56 of the cassette compartment 28 and a displaceable toothed rack 57 of the cassette compartment. Thereby, in a manner known per se, wherein the displaceable toothed rack 57 moves back and forth, the carrier medium holder 15 may be lifted from tooth to tooth of the stationary toothed rack 56 by means of the displaceable toothed rack 57.

A complete biopsy device 43 including a tissue collection device 1 as described above is illustrated in FIGS. 42, 43, 54, 55, 56 and 57. The biopsy device 43 has a housing 44 and a biopsy needle 4 extending from the housing 44. As illustrated in FIGS. 58 and 59, the biopsy needle 4 includes an outer cutting needle 45 and an inner needle 46 with a tissue compartment 3 for receiving a tissue sample 2, wherein the outer cutting needle 45 surrounds the inner needle 46 and is arranged slidingly along the inner needle 46. The outer cutting needle 45 has a cutting end 47 distant from the housing 44 and a sample opening 48 or sample end inside the housing 44 at a distance from the cutting end 47.

The inner needle 46 is slidable in relation to the housing 44 so that the tissue compartment 3 is displaceable between the cutting end 47 of the outer cutting needle 45 and the sample opening 48 or sample end of the outer cutting needle 45, and the tissue collection device 1 is arranged in the housing 44 at the sample opening 48 or sample end of the outer cutting needle 45.

In order to collect tissue samples 2, the biopsy device 43 is adapted to arrange the inner needle 46 in a rotational collection position when the inner needle 46 is so displaced in relation to the housing 44 of the biopsy device that the tissue compartment 3 is located at the sample opening 48 of the outer cutting needle 45. In the rotational collection position, the general extension direction of the bottom wall 11 of the tissue compartment 3 may correspond to the general swiping direction 13 of the swiping element 9 from the collection position 6 and in the direction of the deposition position 8. It is understood that when the tissue compartment 3 of the inner needle 46 is displaced between the cutting end 47 of the outer cutting needle 45 and the sample opening 48 or sample end of the outer cutting needle 45, the inner needle 46 may possibly rotate about its longitudinal axis.

In the embodiments illustrated in FIGS. 48, 49, 54, 55, 56 and 57, the removable carrier medium cassette 17 is arranged on the outside of the housing 44 of the biopsy device 43 which is also the housing 20 of the tissue collection device 1, and the tissue samples 2 arranged side by side on the carrier medium 7 are visible from outside the housing 20 of the tissue collection device 1.

Preferably the swiping element 9 has a swinging radius which is longer than, preferably at least 1.25 times, more preferred at least 1.5 times and most preferred at least the double of the distance between the collection position 6 and the deposition position 8.

EMBODIMENTS

The following embodiments 1 to 31 are disclosed:

1. A tissue collection device 1 for collection of one or more tissue samples 2 from a tissue compartment 3 of a biopsy needle 4, the tissue collection device including a biopsy needle support arrangement 5 adapted to support a biopsy needle 4 so that a tissue compartment 3 extending in a longitudinal direction in the biopsy needle 4 may be located at a collection position 6, and the tissue collection device 1 including a carrier medium 7 adapted to adhere to and carry a tissue sample 2 deposited thereon, the tissue collection device 1 being adapted to advance a carrier medium holder 15 after each deposition of a tissue sample 2 on a part of the carrier medium 7, so that the deposited tissue sample 2 is moved away on said part of the carrier medium 7 from a deposition position 8 and a fresh part of the carrier medium is moved to the deposition position 8, characterised in that the deposition position 8 is permanently spaced from the collection position 6, in that the tissue collection device 1 includes a swiping element 9 adapted to swipe sideward 10 relative to the longitudinal direction through the tissue compartment 3 located at the collection position 6 and in the direction of the deposition position 8 in order to thereby move a tissue sample 2 from the tissue compartment 3 to the carrier medium 7 and to thereby press the tissue sample 2 onto the carrier medium 7 so that the tissue sample 2 is deposited on the carrier medium 7.

2. A tissue collection device according to embodiment 1, wherein the swiping element 9 is adapted to swipe back and forth through the tissue compartment 3.

3. A tissue collection device according to embodiment 1 or 2, wherein the swiping element 9 has the form of an elastic blade.

4. A tissue collection device according to any one of the preceding embodiments, wherein the swiping element 9 is adapted to wipe a bottom wall 11 of the tissue compartment 3 as it swipes through the tissue compartment 3.

5. A tissue collection device according to any one of the preceding embodiments, wherein the swiping element 9 is arranged pivotally 12 in the tissue collection device 1.

6. A tissue collection device according to any one of the preceding embodiments, wherein a general swiping direction 13 of the swiping element 9 from the collection position 6 and in the direction of the deposition position 8 forms a swiping angle A with a general direction 14 of extension of a part of the carrier medium 7 arranged at the deposition position 8, and wherein the swiping angle A is between 30 degrees and 90 degrees, and preferably between 45 degrees and 90 degrees.

7. A tissue collection device according to any one of the preceding embodiments, wherein the tissue collection device 1 is adapted to place a protective sheet 16 on the corresponding part of the carrier medium 7 after each deposition of a tissue sample 2 and advance the protective sheet 16 with the carrier medium holder 15 so that the deposited tissue samples 2 are sandwiched between the carrier medium 7 and the protective sheet 16.

8. A tissue collection device according to any one of the preceding embodiments, wherein the tissue collection device 1 includes a removable carrier medium cassette 17 in which a number of tissue samples 2 may be arranged side by side on the carrier medium 7 in a row extending along an at least substantially straight line 18 or along a curved line 19.

9. A tissue collection device according to embodiment 8, wherein the removable carrier medium cassette 17 is arranged on the outside of a housing 20 of the tissue collection device 1, and wherein, preferably, the tissue samples 2 arranged side by side on the carrier medium 7 are visible from outside the housing 20 of the tissue collection device 1.

10. A tissue collection device according to embodiment 8 or 9, wherein the tissue collection device 1 is adapted to gradually advance a sheet 21 of carrier medium 7 into the removable carrier medium cassette 17 as successive tissue samples 2 are deposited on the sheet 21 of carrier medium 7, and wherein the tissue collection device 1 is preferably adapted to deposit the tissue samples 2 on the sheet 21 of carrier medium 7 outside the removable carrier medium cassette 17.

11. A tissue collection device according to embodiment 10, wherein the advancing direction 22 of the sheet 21 of carrier medium 7 at the deposition position 8 differs from the advancing direction 23 of the sheet of carrier medium at a carrier medium inlet opening 24 of the removable carrier medium cassette 17 by at least 90 degrees, and preferably by at least 120 degrees.

12. A tissue collection device according to embodiment 10 or 11, wherein the carrier medium holder 15 is fixed on a leading edge 25 of the sheet 21 of carrier medium 7 and is removable from the tissue collection device 1 together with the removable carrier medium cassette 17, and wherein the carrier medium holder 15 is adapted to engage releasably with an advance mechanism 26 arranged in the tissue collection device 1.

13. A tissue collection device according to embodiment 8 or 9, wherein the removable carrier medium cassette 17 has the form of a chain 27 composed by a number of mutually hinged cassette compartments 28 each being adapted to receive a single tissue sample 2, and wherein, preferably, neighbouring hinged cassette compartments 28 are adapted to lock together by means of a snap-lock type mechanism 29 in a straight hinge position 30 so that the entire chain 27 of mutually hinged cassette compartments 28 may be locked in a position in which the chain 27 forms an at least substantially straight line.

14. A tissue collection device according to embodiment 13, wherein the tissue collection device 1 is adapted to store at least a part of the chain 27 forming the removable carrier medium cassette 17 in an at least partly rolled-up state 32.

15. A tissue collection device according to embodiment 13 or 14, wherein the cassette compartments 28 are mutually hinged by means of a flexible hinge 31, such as a living hinge.

16. A tissue collection device according to any one of the embodiments 13 to 15, wherein each cassette compartment 28 has a gripper 33 along a first side 34 and a corresponding protrusion 36 along a second side 35, and wherein the gripper 33 of a first cassette compartment 28 is adapted to grip over a corresponding protrusion 36 of a second cassette compartment 28.

17. A tissue collection device according to any one of the embodiments 13 to 16, wherein each cassette compartment 28 has the form of a channel 37 in which the carrier medium may 7 extend.

18. A tissue collection device according to any one of the embodiments 13 to 17, wherein the channel 37 of each cassette compartment 28 is covered by means of a sheet 21 of carrier medium 7.

19. A tissue collection device according to embodiment 18, wherein the sheet 21 of carrier medium 7 is adapted to be pressed at least further into the channel 37 at deposition of a tissue sample 2.

20. A tissue collection device according to embodiment 18 or 19, wherein the channel 37 of each cassette compartment 28 is covered by means of a separate sheet 21 of carrier medium 7.

21. A tissue collection device according to embodiment 20, wherein the separate sheet 21 of carrier medium 7 is fixed along at least one wall 38 of the channel 37 by means of adhesion, such as by means of glue.

22. A tissue collection device according to embodiment 20 or 21, wherein at least one free edge 39 of the separate sheet 21 of carrier medium 7 is held in place in the channel 37 by a corresponding protrusion 40 arranged at a corresponding wall 38 of the channel 37.

23. A tissue collection device according to embodiment 18 or 19, wherein all the channels 37 of the cassette compartments 28 are covered by means of a single common sheet 41 of carrier medium 7.

24. A tissue collection device according to embodiment 23, wherein the single common sheet 41 of carrier medium 7 forms a bulge or crease 42 between neighbouring hinged cassette compartments 28.

25. A tissue collection device according to any one of the preceding embodiments, wherein the carrier medium 7 includes or is formed by a paper material, such as biopsy paper.

26. A tissue collection device according to any one of the preceding embodiments, wherein the biopsy needle support arrangement 5 is adapted to support the biopsy needle 4 relative to a housing 20 of the tissue collection device 1 in a fixed position in a transverse direction of the biopsy needle 4.

27. A biopsy device 43 including a tissue collection device 1 according to any one of the preceding embodiments, wherein the biopsy device 43 has a housing 44 and a biopsy needle 4 extending from the housing 44 and including an outer cutting needle 45 and an inner needle 46 with a tissue compartment 3 for receiving a tissue sample 2, wherein the outer cutting needle 45 surrounds the inner needle 46 and is arranged slidingly along the inner needle 46, wherein the outer cutting needle 45 has a cutting end 47 distant from the housing 44 and a sample opening 48 or sample end inside the housing 44 at a distance from the cutting end 47, wherein the inner needle 46 is slidable in relation to the housing 44 so that the tissue compartment 3 is displaceable between the cutting end 47 of the outer cutting needle 45 and the sample opening 48 or sample end of the outer cutting needle 45, and wherein the tissue collection device 1 is arranged in the housing 44 at the sample opening 48 or sample end of the outer cutting needle 45.

28. A biopsy device according to embodiment 27, wherein the biopsy device 43 is adapted to arrange the inner needle 46 in a rotational collection position when the inner needle 46 is so displaced in relation to the housing 44 of the biopsy device that the tissue compartment 3 is located at the sample opening 48 or sample end of the outer cutting needle 45 for collection of a tissue sample 2, and wherein the rotational collection position corresponds to a general swiping direction 13 of the swiping element 9 from the collection position 6 and in the direction of the deposition position 8.

LIST OF REFERENCE NUMBERS

A swiping angle
1 tissue collection device
2 tissue sample
3 tissue compartment of biopsy needle
4 biopsy needle
5 biopsy needle support arrangement
6 collection position
7 carrier medium
8 deposition position spaced from collection position
9 swiping element
10 sideward relative to longitudinal direction
11 bottom wall of tissue compartment
12 pivotal arrangement of swiping element
13 general swiping direction of swiping element
14 general direction of extension of part of carrier medium
15 carrier medium holder
16 protective sheet
17 removable carrier medium cassette
18 substantially straight line
19 curved line
20 housing of tissue collection device
21 sheet of carrier medium
22 advancing direction of sheet of carrier medium at deposition position
23 advancing direction of sheet of carrier medium at carrier medium inlet opening
24 carrier medium inlet opening
25 leading edge of sheet of carrier medium
26 advance mechanism
27 chain
28 cassette compartment
29 snap-lock type mechanism
30 straight hinge position
31 flexible hinge
32 rolled-up state of chain
33 gripper of cassette compartment
34 first side of cassette compartment
35 second side of cassette compartment
36 protrusion of cassette compartment
37 channel of cassette compartment
38 wall of channel
39 free edge of separate sheet of carrier medium
40 protrusion arranged at side of channel
41 single common sheet of carrier medium
42 crease of carrier medium
43 biopsy device 44 housing of biopsy device
45 outer cutting needle
46 inner needle
47 cutting end of outer cutting needle
48 sample opening of outer cutting needle
49 lid of removable carrier medium cassette
50 spindle of advance mechanism
51 rolled-up sheet of carrier medium
52 spiked wheel of cassette production apparatus
53 support element for protective sheet
54 tab of sheet of carrier medium
55 separate sheet of carrier medium of cassette compartment
56 stationary toothed rack of cassette compartment
57 displaceable toothed rack of cassette compartment
58 support element for sheet of carrier medium
59 displaceable gripper of advance mechanism
60 wall of cassette compartment
61 welding tool
62 punching tool
63 movement of displaceable toothed rack of cassette compartment
64 swiping blade
65 lever arm for swiping blade
66 pin of cassette compartment

The invention claimed is:

1. A tissue collection device for collection of one or more tissue samples from a tissue compartment of a biopsy needle, the tissue compartment extending in a longitudinal direction of the biopsy needle, the tissue collection device comprising:
   a biopsy needle support arrangement adapted to support the biopsy needle so that the tissue compartment is located at a collection position;
   a carrier medium adapted to adhere to and carry a first tissue sample of the one or more tissue samples deposited thereon, the tissue collection device being adapted to advance a carrier medium holder after deposition of the first tissue sample on a part of the carrier medium so that the deposited first tissue sample is moved away on the part of the carrier medium from a deposition position and a fresh part of the carrier medium is moved to the deposition position, wherein the deposition position is permanently spaced from the collection position; and
   a swiping element pivotably arranged in the tissue collection device, the swiping element adapted to swipe sideward relative to the longitudinal direction through the tissue compartment located at the collection position and in a direction of the deposition position to (i) thereby move the first tissue sample from the tissue compartment to the carrier medium and to (ii) thereby press the first tissue sample onto the carrier medium so that the first tissue sample is deposited on the carrier medium.

2. A tissue collection device according to claim 1, wherein the swiping element is adapted to swipe back and forth through the tissue compartment.

3. A tissue collection device according to claim 1, wherein the swiping element includes an elastic blade.

4. A tissue collection device according to claim 1, wherein the swiping element is adapted to wipe a bottom wall of the tissue compartment as the swiping element swipes through the tissue compartment.

5. A tissue collection device according to claim 1, wherein a general swiping direction of the swiping element from the collection position toward the deposition position forms a swiping angle with a general direction of extension of the part of the carrier medium arranged at the deposition position, and wherein the swiping angle is between 30 degrees and 90 degrees or between 45 degrees and 90 degrees.

6. A tissue collection device according to claim 1, wherein the tissue collection device is adapted to place a protective sheet on the carrier medium after the deposition of the first tissue sample and advance the protective sheet with the carrier medium holder so that the deposited first tissue sample is sandwiched between the carrier medium and the protective sheet.

7. A tissue collection device according to claim 1, wherein the tissue collection device further includes the carrier medium holder, the carrier medium holder including a removable carrier medium cassette in which the first tissue sample and at least a second tissue sample of the one or more tissue samples are arranged side by side on the carrier medium in a row extending along a straight line or along a curved line.

8. A tissue collection device according to claim 7, wherein the removable carrier medium cassette is arranged outside of a housing of the tissue collection device, and wherein the first and second tissue samples arranged side by side on the carrier medium are visible from outside the housing of the tissue collection device.

9. A tissue collection device according to claim 7, wherein the carrier medium includes a sheet, the tissue collection device is adapted to gradually advance the sheet of the carrier medium into the removable carrier medium cassette as the first and second tissue samples are successively deposited on the sheet of the carrier medium, and wherein the tissue collection device is adapted to deposit the first and second tissue samples on the sheet of the carrier medium outside the removable carrier medium cassette.

10. A tissue collection device according to claim 9, wherein a first advancing direction of the sheet of the carrier medium at the deposition position differs from a second advancing direction of the sheet of the carrier medium at a carrier medium inlet opening of the removable carrier medium cassette by at least 90 degrees.

11. A tissue collection device according to claim 9, wherein the carrier medium holder is fixed on a leading edge of the sheet of the carrier medium, and wherein the carrier medium holder is adapted to engage releasably with an advance mechanism arranged in the tissue collection device.

12. A tissue collection device according to claim 7, wherein the removable carrier medium cassette has a form of a chain composed of a plurality of mutually hinged cassette compartments each of which is configured to receive the first tissue sample, the second tissue sample, or another tissue sample, and wherein neighbouring ones of the plurality of mutually hinged cassette compartments are adapted to lock together by a snap-lock type mechanism in a straight hinge position so that the plurality of mutually hinged cassette compartments are locked in a position in which the chain forms a straight line.

13. A tissue collection device according to claim 1, wherein the biopsy needle support arrangement is adapted to support the biopsy needle relative to a housing of the tissue collection device in a fixed position in a transverse direction of the biopsy needle.

14. A biopsy device including a tissue collection device according to claim 1, wherein the biopsy device has a housing and a biopsy needle extending from the housing and including an outer cutting needle and an inner needle, the inner needle including the tissue compartment for receiving the first tissue sample, wherein the outer cutting needle surrounds the inner needle and is arranged slidingly along the inner needle, wherein the outer cutting needle has a cutting end distant from the housing and a sample opening or sample end inside the housing at a distance from the cutting end, wherein the inner needle is slidable in relation to the housing so that the tissue compartment is displaceable between the cutting end of the outer cutting needle and the sample opening or sample end of the outer cutting needle, and wherein the tissue collection device is arranged in the housing at the sample opening or sample end of the outer cutting needle.

15. A tissue collection device for collection of one or more tissue samples from a tissue compartment of a biopsy needle, the tissue compartment extending in a longitudinal direction of the biopsy needle, the tissue collection device comprising:
- a biopsy needle support arrangement adapted to support the biopsy needle so that the tissue compartment is located at a collection position;
- a carrier medium adapted to adhere to and carry a first tissue sample of the one or more tissue samples deposited thereon, the tissue collection device being adapted to advance a carrier medium holder after deposition of the first tissue sample on a part of the carrier medium so that the deposited first tissue sample is moved away on the part of the carrier medium from a deposition position and a fresh part of the carrier medium is moved to the deposition position, wherein the deposition position is permanently spaced from the collection position; and
- a swiping element adapted to swipe sideward relative to the longitudinal direction through the tissue compartment located at the collection position and in a direction of the deposition position to (i) thereby move the first tissue sample from the tissue compartment to the carrier medium and (ii) thereby press the first tissue sample onto the carrier medium so that the first tissue sample is deposited on the carrier medium, wherein a general swiping direction of the swiping element from the collection position toward the deposition position forms a swiping angle with a general direction of extension of the part of the carrier medium arranged at the deposition position, and wherein the swiping angle is between 30 degrees and 90 degrees or between 45 degrees and 90 degrees.

16. A tissue collection device for collection of first and second tissue samples from a tissue compartment of a biopsy needle, the tissue compartment extending in a longitudinal direction of the biopsy needle, the tissue collection device comprising:
- a biopsy needle support arrangement adapted to support the biopsy needle so that the tissue compartment is located at a collection position;
- a carrier medium holder including a removable carrier medium cassette;
- a carrier medium adapted to adhere to and carry the first tissue sample deposited thereon, the tissue collection device being adapted to advance the carrier medium holder after deposition of the first tissue sample on a part of the carrier medium so that the deposited first tissue sample is moved away on the part of the carrier medium from a deposition position and a fresh part of the carrier medium is moved to the deposition position for receiving the second tissue sample, wherein the deposition position is permanently spaced from the collection position, and wherein the first tissue sample and the second tissue sample carried by the carrier medium are arranged on the removable carrier medium cassette in a side by side arrangement in a row extending along a straight line or along a curved line; and
- a swiping element adapted to swipe sideward relative to the longitudinal direction through the tissue compartment located at the collection position and in a direction of the deposition position to (i) thereby move the first tissue sample from the tissue compartment to the carrier medium and (ii) thereby press the first tissue sample onto the carrier medium so that the first tissue sample is deposited on the carrier medium;
- wherein the carrier medium includes a sheet, the tissue collection device is adapted to gradually advance the sheet of the carrier medium into the removable carrier medium cassette as the first and second tissue samples are successively deposited on the sheet of the carrier medium, and wherein the tissue collection device is adapted to deposit the first and second tissue samples on the sheet of the carrier medium outside the removable carrier medium cassette.

17. A tissue collection device according to claim 16, wherein a first advancing direction of the sheet of the carrier medium at the deposition position differs from a second advancing direction of the sheet of the carrier medium at a carrier medium inlet opening of the removable carrier medium cassette by at least 90 degrees.

18. A tissue collection device according to claim 16, wherein the carrier medium holder is fixed on a leading edge of the sheet of the carrier medium, and wherein the carrier medium holder is adapted to engage releasably with an advance mechanism arranged in the tissue collection device.

19. A tissue collection device for collection of first and second tissue samples from a tissue compartment of a biopsy needle, the tissue compartment extending in a longitudinal direction of the biopsy needle, the tissue collection device comprising:
- a biopsy needle support arrangement adapted to support the biopsy needle so that the tissue compartment is located at a collection position;
- a carrier medium holder including a removable carrier medium cassette;
- a carrier medium adapted to adhere to and carry the first tissue sample deposited thereon, the tissue collection device being adapted to advance the carrier medium holder after deposition of the first tissue sample on a part of the carrier medium so that the deposited first tissue sample is moved away on the part of the carrier medium from a deposition position and a fresh part of the carrier medium is moved to the deposition position for receiving the second tissue sample, wherein the deposition position is permanently spaced from the collection position, and wherein the first tissue sample and the second tissue sample carried by the carrier medium are arranged on the removable carrier medium cassette in a side by side arrangement in a row extending along a straight line or along a curved line; and
- a swiping element adapted to swipe sideward relative to the longitudinal direction through the tissue compartment located at the collection position and in a direction of the deposition position to (i) thereby move the first tissue sample from the tissue compartment to the carrier medium and (ii) thereby press the first tissue sample onto the carrier medium so that the first tissue sample is deposited on the carrier medium;
- wherein the removable carrier medium cassette has a form of a chain composed of a plurality of mutually hinged cassette compartments, a first one and a second one of the plurality of mutually hinged cassette compartments are configured to receive, respectively, the first tissue sample and the second tissue sample, and wherein neighbouring ones of the plurality of mutually hinged cassette compartments are adapted to lock together by a snap-lock type mechanism in a straight hinge position so that the plurality of mutually hinged cassette compartments are locked in a position in which the chain forms a straight line.

\* \* \* \* \*